US008637044B2

(12) United States Patent
Barnett et al.

(10) Patent No.: US 8,637,044 B2
(45) Date of Patent: Jan. 28, 2014

(54) METHOD OF GENERATING AN IMMUNE RESPONSE IN A SUBJECT USING FUSION PROTEINS COMPRISING CD4 MINIMAL MODULES AND HIV TAT SCAFFOLD POLYPEPTIDES THAT ARE CAPABLE OF BINDING TO THE HIV ENVELOPE AND EXPOSING CRYPTIC NEUTRALIZATION EPITOPES

(75) Inventors: Susan Barnett, Emeryville, CA (US); Rino Rappuoli, Siena (IT); Victoria A Sharma, Emeryville, CA (US); Indresh K Srivastava, Emeryville, CA (US); Jan Zur Megede, Emeryville, CA (US)

(73) Assignee: Novartis AG, Basel (CH)

( * ) Notice: Subject to any disclaimer, the term of this patent is extended or adjusted under 35 U.S.C. 154(b) by 19 days.

(21) Appl. No.: 13/427,234

(22) Filed: Mar. 22, 2012

(65) Prior Publication Data
US 2012/0183557 A1 Jul. 19, 2012

Related U.S. Application Data

(62) Division of application No. 11/883,696, filed as application No. PCT/US2006/003935 on Feb. 3, 2006, now Pat. No. 8,168,194.

(60) Provisional application No. 60/650,635, filed on Feb. 3, 2005.

(51) Int. Cl.
*A61K 39/21* (2006.01)
*A61K 39/00* (2006.01)
*A61K 39/385* (2006.01)
*C07K 1/00* (2006.01)

(52) U.S. Cl.
USPC ............... 424/192.1; 424/196.11; 424/208.1; 530/350

(58) Field of Classification Search
None
See application file for complete search history.

(56) References Cited

U.S. PATENT DOCUMENTS

| | | | |
|---|---|---|---|
| 4,708,871 | A | 11/1987 | Geysen |
| 5,518,723 | A | 5/1996 | DeVico et al. |
| 5,714,316 | A | 2/1998 | Weiner et al. |
| 5,843,454 | A | 12/1998 | Devico et al. |
| 6,004,781 | A | 12/1999 | Seed et al. |
| 6,030,772 | A | 2/2000 | Devico et al. |
| 6,117,656 | A | 9/2000 | Seed |

(Continued)

FOREIGN PATENT DOCUMENTS

| | | |
|---|---|---|
| WO | 9419017 A1 | 9/1994 |
| WO | 9604301 A2 | 2/1996 |

(Continued)

OTHER PUBLICATIONS

Pejchal, R., and I. A. Wilson, 2010, Structure-based vaccine design in HIV: blind men and the elephant? Curr. Pharm. Des. 16(33):3744-3753.*

(Continued)

*Primary Examiner* — Jeffrey S. Parkin
(74) *Attorney, Agent, or Firm* — Regina Bautista; Helen Lee

(57) ABSTRACT

Hybrid molecules comprising CD4 minimal modules or mimetics that bind to HIV Env polypeptides in combination with one or more HIV Tat polypeptides are described. Also described are complexes of these hybrid molecules with Env as well as methods of diagnosis, treatment and prevention using the polynucleotides and polypeptides.

20 Claims, 7 Drawing Sheets

KKVVLGKKGDTVELTCTASQKKSIQFHWKNSNQIKILGNQGSFLTKGPSKLNDRADSRR
SLWDQGNFPLIIKNLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKVEFKIDIVVLAFQ
KASSIVYKKEGEQVEFSFPLAFTVEKLTGSGELWWQAERASSSKSWITFDLKNKEVSVK
RVTQDPKLQMGKKLPLHLTLPQALPQYAGSGNLTLALEAKTGKLHQEVNLVVMRATQ
LQKNLTCEVWGPTSPKLMLSLKLENKEAKVSKREKAVWVLNPEAGMWQCLLSDSGQV
LLESNIKVLPTWSTPVQPMALIVLGGVAGLLLFIGLGIFFCVRCRHRRRQAERMSQIKRL
LSEKKTCQCPHRFQKTCSPI (SEQ ID NO: 1)

(56) References Cited

U.S. PATENT DOCUMENTS

| | | | |
|---|---|---|---|
| 7,811,580 | B2 | 10/2010 | Barnett et al. |
| 8,206,720 | B2 * | 6/2012 | Masignani et al. ........ 424/192.1 |
| 2002/0177551 | A1 | 11/2002 | Terman |
| 2008/0317779 | A1 | 12/2008 | Barnett et al. |
| 2010/0183653 | A1 | 7/2010 | Masignani et al. |

FOREIGN PATENT DOCUMENTS

| | | |
|---|---|---|
| WO | 0039302 A2 | 7/2000 |
| WO | 0039303 A2 | 7/2000 |
| WO | 0130814 A1 | 5/2001 |
| WO | 03020876 A2 | 3/2003 |
| WO | 2004014420 A1 | 2/2004 |
| WO | 2004037847 A2 | 5/2004 |

OTHER PUBLICATIONS

ISR dated Jun. 19, 2008, in the international application PCT/US05/22801

Agwale et al., (Jul. 23, 2002) "A Tat subunit vaccine confers protective immunity against the immune-modulating activity of the human immunodeficiency virus type-1 Tat protein in mice", Proceedings of the National Academy of Sciences of USA, National Academy of Science, Washington, DC, US, vol. 99, No. 15, pp. 10037-10041, XP002226223, ISSN: 0027-8424.

Al-Jaufy et al., (1994) "Cytotoxicity of a Shiga toxin A subunit-CD4 fusion protein to human immunodeficiency virus-infected cell", Infect. Immun., vol. 62, No. 3, pp. 956-960.

Arthos et al., (1989) "Identification of the Residues in Human CD4 Critical for the Binding of HIV", Cell 57: 469-81.

Ashkenazi, A. et al., (1990) "Mapping the CD4 binding site for human immunodeficiency virus by alanine-scanning mutagenesis", Proc. Natl. Acad. Sci., USA 87: 7150-7154.

Aullo et al., (1992) "A recombinant diptheria toxin related human CD4 fusion protein specifically kills HIV infected cells which express gp120 but selects fusion toxin resistant cells which carry HIV", Embo J., vol. 11, No. 2, pp. 575-583.

Barre-Sinoussi et al., (1983) "Isolation of a T-Lymphotropic Retrovirus from a Patient at Risk for Acquired Immune Deficiency Syndrome (AIDS)", Science 220: 868-71.

Binley et al., (1997) "An Investigation of the High_Avidity Antibody Response to Glycoprotein 120 of Human Immunodeficiency Virus Type 1", AIDS Res. Hum. Retroviruses 13: 1007-15.

Bolognesi et al., (1994) "HIV Vaccine Development: A Progress Report", Ann. Int. Med. 8: 603-11.

Bower et al., (Oct. 25, 2004) "DNA vaccines expressing soluble CD4-envelope proteins fused to C3d elicit cross-reactive neutralizing antibodies to HIV-1," Virology, Academic Press, Orlando, vol. 328, No. 2, pp. 292-300. XP004581382, ISSN: 0042-6822.

Burton, D.R. et al., (2004) "HIV vaccine design and the neutralizing antibody problem", Nat. Immunol., 5(3): p. 233-236.

Burton & Montefiore, (1997) "The antibody response in HIV-1 infection", AIDS 11 (Suppl. A): 587-98.

Clackson & Wells, (1995) "A Hot Spot of Binding Energy in a Hormone-Receptor Interface", Science 267: 383-86.

Dash, B. et al., (1994) "Deletion of a single N-linked glycosylation site from the transmembrane envelope protein of human immunodeficiency virus type 1 stops cleavage and transport of gp160 preventing env-mediated fusion", J. Gen. Virol., 75(6): 1389-1397.

Davio et al., (1995) Interdomain Interactions in the Chimeric Protein Toxin sCD4(178)-PE40: A Differential Scanning calorimetry (DSC) Study, Pharmaceutical Research, vol. 12, No. 5, pp. 642-648, XP008024188.

Devico et al., (1995) "Monoclonal Antibodies Raised Against Covalently Crosslinked of Human Immunodeficiency Type 1 gp120 and CD4 Receptor Identify a Novel Complex-Dependent Epitope on gp120", Virol. 211: 583-88.

Devico et al., (1996) "Covalently Crosslinked Complexes of Human Immunodeficiency Virus Type 1 (HIV-1) gp120 and CD4 Receptor Elicit a Neutralizing Immune Response That Includes Antibodies Selective for Primary Virus Isolates", Virology 218: 258-63.

Dey, B. et al., (2003) "Neutralization of human immunodeficiency virus type 1 by sCD4-17b, a single-chain chimeric protein, based on sequential interaction of gp120 with CD4 and coreceptor", J. Virol., 77(5): 2859-2865.

D'Souza et al., (1997) "Evaluation of Monoclonal Antibodies to Human Immunodeficiency Virus Type 1 Promary Isolates by Neutralization Assays: Performance Criteria for Selecting Candidate Antibodies for Clinical Trials", J. Infect. Dis. 75: 56-62.

Fiore et al., (1994) "The Biological Phenotype of HIV-1 is Usually Retained During and After Sexual Transmission", Virol. 204: 297-303.

Fouts et al., "Crosslinked HIV-1 envelope-CD4 receptor complexes elicit broadly cross-reactive neutralizing antibodies in rhesus macaques," Proc Natl Acad Sci U S A. Sep. 3, 2002;99(18):11842-7. Epub Aug. 21, 2002.

Gallo et al., (1984) "Frequent Detection and Isolation of cytopathic Retroviruses (HTL V-III) from Patients with AIDS and at Risk for AIDS", "Serological Analysis of a Subgroup of Human T-Lymphotropic Retroviruses (HTL V-III) Associated with Aids"; Science 224: 500-03.

Gallo, R.C. et al., (2005) "The end of the beginning of the drive to an HIV-preventive vaccine: A view from over 20 years", The Lancet 366:1894-1898.

Database PIR Entry A03976 (Entry VCLJA2), May 17, 1985.

Gershoni et al., (1993) "HIV Binding to Its Receptor Creates Specific Epitopes for the CD4/gp120 Complex", FASEB J. 7: 1185-87.

Geysen et al., (1984) "Use of peptide synthesis to probe viral antigens for epitopes to a resolution of a single amino acid", Proc. Natl. Acad. Sci., USA 81: 3998-4002.

Geysen et al., (1986) "A Priori Delineation of a Peptide Which Mimics a Discontinuous Antigenic Determinant", Mol. Immunol. 23: 709-15.

Guyader et al., (1987) "Genome Organization and Transactivation of the Human Immunodeficiency Virus Type 2", Nature 326: 662-69.

Haynes et al., (1996) "Toward an Understanding of the Correlates of Protective Immunity to HIV Infection", Science 271: 327-28.

Hu et al., (1992) "Protection of Macaques Against SIV Infection by Subunit Vaccines of SIV Envelope Glycoprotein gp160", Science 255: 456-59.

Javaherian et al., (1989) "Principal neutralizing domain of the human immunodeficiency virus type 1 envelope protein", Proc. Natl. Acad. Sci., USA 86: 6786-72.

Kwong et al., (1998) "Structure of an HIV gp120 envelope glycoprotein in complex with the CD4 receptor and a neutralizing human antibody", Nature 393: 648-59.

Lacasset et al., (1999) "Fusion-Competent Vaccines: Broad Neutralizations of Primary Isolates of HIV", Science 283: 357-62.

Leong et al., (1990) "Identification of the integrin binding domain of the *Yersinia psudotuberculosis* invasion protein," The Embo Journal, vol. 9, No. 6, pp. 1979-1989, XP008119834.

Levy et al., (1984) "Isolation of Lymphocytopathic Retroviruses from San Francisco Patients with AIDS", Science 225: 840-42.

Linhart et al., (Aug. 4, 2004) "Vaccine engineering improved by hybrid technology," International Archives of Allergy and Immunology, vol. 134, No. 4, pp. 324-331, XP009072133, ISSN: 1018-2438.

Lu, S. et al., (1998) "Immunogenicity of DNA vaccines expressing human immunodeficiency virus type 1 envelope glycoprotein with and without deletions in the V1/2 and V3 regions", AIDS Res. Human Retrovir., 14(2): 151-5.

Martin et al., (2003) "Rational Design of a CD4 Mimic that Inhibits HIV-1 Entry and Exposes Cryptic Neutralization Epitopes"; Nat. Biotech. 21: 71-76.

Mascola et al., (1996) "Immunization with Envelope Subunit Vaccine Products Elicits Neutralizing Antibodies against Laboratory-Adapted but not Primary Isolates of Human Immunodeficiency Virus Type 1", J. Infect. Dis. 173: 340-48.

Matsushita et al., (1988) "Characterization of a Human Immunodeficiency Virus Neutralizing Monoclonal Antibody and Mapping of the Neutralizing Epitope", J. Virol. 62: 2107-44.

(56) References Cited

OTHER PUBLICATIONS

Matthews, (1986) "Restricted neutralization of divergent human T-lymphotropic virus type III isolates by antibodies to the major envelope glycoprotein", Proc. Natl. Acad. Sci. USA 83: 9709-13.
Montefiori & Evans, (1999) "Toward an HIV Type 1 Vaccine that Generates Potent, Broadly Cross-Reactive Neutralizing Antibodies", AIDS Res. Hum. Retroviruses 15: 689-98.
Nara et al., (1988) "Purified Envelope Glycoproteins from Human Immunodeficiency Virus Type 1 Variants Induce Individual, Type-Specific Neutralizing Antibodies", J. Virol. 62: 2622-28.
Palker et al., (1988) "Type-specific neutralization of the human immunodeficiency virus with antibodies to env-encoded synthetic peptides", Proc. Natl. Acad. Sci. USA 85: 1932-36.
Putney et al., (1986) "HTLV-III/LAV-Neutralizing Antibodies to an *E. coli*-Produced Fragment of the Virus Envelope", Science 234: 1392-95.
Ratner et al., (1985) "Complete Nucleotide of the AIDS Virus, HTLV-III", Nature 313: 277-84.
Rizzuto et al., (1998) "A Conserved HIV gp120 Glycoprotein Structure Involved in Chemokine Receptor Binding", Science 280: 1949-53.
Robert-Guroff et al., (1985) "HTLV-III-Neutralizing Antibodies in Patients with AIDS and AIDS-Related Complex", Nature 316: 72-73.
Rushe et al., (1988) "Antibodies that inhibit fusion of human immunodeficiency virus-infected cells bind a 24-amino acid sequence of the viral envelope, gp120", Proc. Natl. Acad. Sci. USA 85: 3198-202.
Ryu et al., (1994) "Structures of an HIV and MHC binding fragment from human CD4 as refined in two crystal lattices", Structure 2: 59-74.
Sanchez-Pescador et al., (1985) "Nucleotide Sequence and Expression of an AIDS-Associated Retrovirus (ARV-2)", Science 227: 484-92.
Siegal et al., (1981) "Severe Acquired Immunodeficiency in male Homosexuals, manifested by Chronic Perianal Ulcerative Herpes Simplex Lesions", N. Engl. J. Med. 305: 1439-44.
Stamatatos & Cheng-Mayer, (1998) "An Envelope Modification That Renders a primary, neutralization-Resistant Clade B Human Immunodeficiency Virus Type 1 Isolate Highly Susceptible to Neutralization by Sera from Other Clades", J. Virol. 72: 7840-45.
Stamatatos et al., (1998) "Effect of major Deletions in the V1 and V2 Loops of a Macrophage-Tropic HIV Type 1 Isolate on Viral Envelope Structure, Cell Entry and Replication", Aids Res. Hum. Retroviruses 14, 1129-39.
Sullivan et al., (1998) "Determinants of Human Immunodeficiency Virus Type 1 Envelope Clycoprotein Activation by Soluble CD4 and Monoclonal Antibodies", J. Virol. 72: 6332-38.
Thali et al., (1993) "Characterization of Conserved Human Immunodeficiency virus Type 1 gp120 Neutralization Epitopes Exposed upon gp120-CD4 Binding", J. Virol. 67: 3978-88.
Trkola et al., (1995) "Cross-Clade Neutralization of Primary Isolates of Human Immunodeficiency Virus Type 1 by Human Monocolonal Antibodies and Tetrameric CD4-IgG", J. Virol. 69: 6609-17.
Truneh et al., (1991) "A Region in Domain 1 of CD4 Distinct from the Primary gp120 Binding Site Is Involved in HIV Infection and Virus-mediated Fusion", J. Biol. Chem. 266: 5942-48.
Vita et al., (1998) "Novel Miniproteins Engineered by the Transfer of Active Sites to Small Natural Scaffolds", Biopolymers 47: 93-100.
Vita et al., (1999) "Rational engineering of a miniprotein that reproduces the core of the CD4 site interacting with HIV-1 envelope glycoprotein", Proc. Natl. Acad. Sci. USA 96: 13091-96.
Vu et al., (2006) "An Immunoglobulin Fusion Protein Based on the gp120-CD4 Receptor complex Potently Inhibits Human Immunodeficiency Virus Type 1 in Vitro", AIDS Res. Human Retroviruses 22: 477-90.
Wang et al., (Nov. 22, 2002) "Synthetic AIDS vaccine by targeting HIV receptor," Vaccine, Butterworth Scientific, Guildford, GB, vol. 21, No. 1-2, pp. 89-97, XP004393289, ISSN: 0264-410X.
Weis et al., (1985) "Neutralization of Human T-Lymphotropic Virus Type III by Sera of AIDS and AIDS-Risk Patients", Nature 316: 69-72.
Weis et al., (1986) "Variable and Conserved Neutralization Antigens of Human Immunodeficiency Virus", Nature 324: 572-75.
Wu et al., (1996) "Kinetic and structural analysis of mutant CD4 receptors that are defective in HIV gp120 binding", Proc. Natl. Acad. Sci. USA, No. 93, pp. 15030-15035.
Wyatt et al., (1995) "Involvement of the V1/V2 Variable Loop Structure in the Exposure of Human Immunodeficiency Virus Type 1 gp120 Epitopes Induced by Receptor Binding", J. Virol. 69: 5723-33.
Wyatt et al., (1998) "The antigenic structure of the HIV gp120 envelope glycoprotein", Nature 393: 705-11.
Xiao, X. et al., (2003) "Purified complexes of HIV-1 envelope glycoproteins with CD4 and CCR5(CXCR4): production, characterization, and immunogenicity", Vaccine 21: 4275-4284.
Zagury et al., (1986) "Long-Term Cultures of HTLV-III-Infected T Cells: A Model of Cytopathology of T-Cell Depletion in AIDS", Science 231: 850-53.
Zettlmeissl et al., (1990) "Expression and characterization of human CD4: immunoglobulin fusion domains", DNA Cell Biol., vol. 9, No. 5, pp. 347-353.
Zhang et al., (1999) "Conformational Changes of gp120 in Epitopes near the CCR5 Binding Site Are Induced by CD4 and a CD4 Miniprotein Mimetic", Biochemistry 38: 9405-16.
Zhu et al., (1993) "Genotypic and Phenotypic Characterization of HIV-1 in Patients with Primary Infection", Science, 261: 1179-81.
Cordonnier et al., (Aug. 17, 1989) "Single amino-acid changes in HIV envelope affect viral tropism and receptor binding," Nature., 340(6234): 571-574.
Lasky et al., (Sep. 11, 1987) "Delineation of a region of the human immunodeficiency virus type 1 gp120 glycoprotein critical for interaction with the CD4 receptor," Cell., 50(6): 975-85.

\* cited by examiner

KKVVLGKKGDTVELTCTASQKKSIQFHWKNSNQIKILGNQGSFLTKGPSKLNDRADSRR
SLWDQGNFPLIIKNLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKVEFKIDIVVLAFQ
KASSIVYKKEGEQVEFSFPLAFTVEKLTGSGELWWQAERASSSKSWITFDLKNKEVSVK
RVTQDPKLQMGKKLPLHLTLPQALPQYAGSGNLTLALEAKTGKLHQEVNLVVMRATQ
LQKNLTCEVWGPTSPKLMLSLKLENKEAKVSKREKAVWVLNPEAGMWQCLLSDSGQV
LLESNIKVLPTWSTPVQPMALIVLGGVAGLLLFIGLGIFFCVRCRHRRRQAERMSQIKRL
LSEKKTCQCPHRFQKTCSPI (SEQ ID NO: 1)

FIG. 1

MEPVDPRLEPWKHPGSQPKTACTNCYCKKCCFHCQVCFITKALGISYGRKKRRQRRRA
HQNSQTHQASLSKQPTSQPRGDPTGPKE (SEQ ID NO: 2)

FIG. 2

MEPVDPRLEPWKHPGSQPKTACTNCYCKKCCFHCQVCFITKGLGISYGRKKRRQRRRA
PPDSEVHQVSLPKQPASQPQGDPTGPKESKKKVERETETDPVH (SEQ ID NO: 3)

FIG. 3

Design chimeric molecule consisting of TAT "scaffold" and minimal env binding module of CD4

| 1 – 20 | 30 | – | 86 |     Residues 21-29
| TAT | CD4 min domain | TAT |

| 1 | – 30 | 40 | – | 86 |     Residues 31-39
| TAT | CD4 min domain | TAT |

| 1 | – 40 | 50 | – | 86 |     Residues 41-49
| TAT | CD4 min domain | TAT |

| 1 | – 50 | 60-86 |     Residues 51-59
| TAT | CD4 min domain | TAT |

FIG. 5

Tat Bru deletions + min CD4 binding region

1-20Δ21-29(ACTTCYCKK)
MEPVDPRLEPWKHPGSQPKTtctasqkksiqfhwknsnqikilgnqgsfltkgpsklndradsrrslwdqgn
fpliiknlkiedsdtyiceCCFHCQVCFTTKALGISYGRKKRRQRRRPPQGSQTHQVSLSKQPTSQPRG
DPTGPKE

1-30Δ31-39(CFHCQVCFT)
MEPVDPRLEPWKHPGSQPKTACTTCYCKKCtctasqkksiqfhwknsnqikilgnqgsfltkgpsklndr
adsrrslwdqgnfpliiknlkiedsdtyiceKALGISYGRKKRRQRRRPPQGSQTHQVSLSKQPTSQPRG
DPTGPKE

1-40Δ41-49(KALGISYGR)
MEPVDPRLEPWKHPGSQPKTACTTCYCKKCCFHCQVCFTTtctasqkksiqfhwknsnqikilgnqgsfl
tkgpsklndradsrrslwdqgnfpliiknlkiedsdtyiceKKRRQRRRPPQGSQTHQVSLSKQPTSQPRG
DPTGPKE

1-50Δ51-59(KRRQRRRPP)
MEPVDPRLEPWKHPGSQPKTACTTCYCKKCCFHCQVCFTTKALGISYGRKtctasqkksiqfhwknsnq
ikilgnqgsfltkgpsklndradsrrslwdqgnfpliiknlkiedsdtyiceQGSQTHQVSLSKQPTSQPRG
DPTGPKE

FIG. 6

Tat SF162 deletions + min CD4 binding region 1-20Δ21-29(ACTNCYCKK)
MEPVDPRLEPWKHPGSQPKTtctasqkksiqfhwknsnqikilgnqgsfltkgpsklndradsrrs
lwdqgnfpliiknlkiedsdtyiceCCFHCQVCFITKGLGISYGRKKRRQRRRAPPDSEVHQVSLP
KQPASQPQGDPTGPKE 1-30Δ31-39(CFHCQVCFI)
MEPVDPRLEPWKHPGSQPKTACTNCYCKKCtctasqkksiqfhwknsnqikilgnqgsfltkgpsk
lndradsrrslwdqgnfpliiknlkiedsdtyiceTKGLGISYGRKKRRQRRRAPPDSEVHQVSLP
KQPASQPQGDPTGPKE 1-40Δ41-49(KGLGISYGR)
MEPVDPRLEPWKHPGSQPKTACTNCYCKKCCFHCQVCFITtctasqkksiqfhwknsnqikilgnq
gsfltkgpsklndradsrrslwdqgnfpliiknlkiedsdtyiceKKRRQRRRAPPDSEVHQVSLP
KQPASQPQGDPTGPKE 1-50Δ51-59(KRRQRRRAP)
MEPVDPRLEPWKHPGSQPKTACTNCYCKKCCFHCQVCFITKGLGISYGRKtctasqkksiqfhwkn
snqikilgnqgsfltkgpsklndradsrrslwdqgnfpliiknlkiedsdtyicePDSEVHQVSLP
KQPASQPQGDPTGPKE

FIG. 7

Alignment Tat Bru vs SF162

```
                   1                                                50
aaTatBru   (1)   MEPVDPRLEPWKHPGSQPKTACTTCYCKKCCFHCQVCFITKALGISYGRK
aaTatSF162 (1)   MEPVDPRLEPWKHPGSQPKTACTNCYCKKCCFHCQVCFITKGLGISYGRK aaTatBru   (51)  KKRQRRRPPQGSQTHQVSLSKQPTSQPRGDPTGPKE-----------
aaTatSF162 (51)  KKRQRRRAPPDSEVHQVSLPKQPASQPQGDPTGPKESKKKVERETETDPV aaTatBru   (87)  -
aaTatSF162 (101) H
```

FIG. 8

METHOD OF GENERATING AN IMMUNE RESPONSE IN A SUBJECT USING FUSION PROTEINS COMPRISING CD4 MINIMAL MODULES AND HIV TAT SCAFFOLD POLYPEPTIDES THAT ARE CAPABLE OF BINDING TO THE HIV ENVELOPE AND EXPOSING CRYPTIC NEUTRALIZATION EPITOPES

CROSS-REFERENCE TO RELATED APPLICATIONS

This application is a divisional of U.S. application Ser. No. 11/883,696, filed Jul. 22, 2008, now allowed, which is a U.S. National Stage application under 35 U.S.C. §371 of International Application PCT/US2006/003935 (published as WO 2006/084179 A3), filed Feb. 3, 2006, which claims priority to U.S. Provisional Application Ser. No. 60/650,635, filed Feb. 3, 2005. Benefit of the filing date of each of these prior applications is hereby claimed. Each of these prior applications is hereby incorporated by reference in its entirety.

STATEMENT OF GOVERNMENT SUPPORT

The invention was supported, in whole or in part, by NIAID-NIH HIVRAD under Grant No. 5 P01 AI-48225-03 from the National Institute of Allergy and Infectious Diseases. The U.S. Government has certain rights in the invention.

This application incorporates by reference the contents of a 18.2 kb text file created on Mar. 22, 2012 and named "PAT051798DIVsequencelisting.txt," which is the sequence listing for this application.

TECHNICAL FIELD

The invention relates generally to immunogenic compositions comprising at least a portion of an HIV Tat polypeptide and a CD4 molecule (e.g., CD4 minimal module, CD4 mimetic, etc.). The immunogenic compositions described herein bind to HIV Env proteins (such as monomeric or oligomeric gp120, gp140 or gp160) and induce a conformational change in the Env protein such that conserved, cryptic and functional epitopes are exposed. The invention also pertains to methods of using these immunogenic compositions as part of a unimolecular or bimolecular complex with HIV Env polypeptide to elicit an immune response against a broad range of HIV subtypes.

BACKGROUND

The human immunodeficiency virus (HIV-1, also referred to as HTLV-III, LAV or HTLV-III/LAV) is the etiological agent of the acquired immune deficiency syndrome (AIDS) and related disorders (see, e.g., Barre-Sinoussi, et al., (1983) Science 220:868-871; Gallo et al. (1984) Science 224:500-503; Levy et al., (1984) Science 225:840-842; Siegal et al., (1981) N. Engl. J Med. 305:1439-1444; Guyader et al., (1987) Nature 326:662-669).

The envelope protein of HIV-1, HIV-2 and SIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells. Furthermore, upon binding to its receptor, CD4, the Env polypeptide undergoes a significant structural rearrangement. After this conformational change a CCR5 or other chemokine binding co-receptor binding site is exposed. Exposure of this chemokine receptor binding site, in turn, mediates viral entry into the host cell. See, e.g., Wyatt, R. et al. (1998) Nature 393:705-711; Kwong, P. et al. (1998) Nature 393:648-659.

Env appears to be the primary target for inducing a humoral immune response to HIV. However, it is known that antibodies directed against gp120 do not generally exhibit broad antibody responses against different HIV strains and gp120 alone does not induce production of broadly neutralizing antibodies. See, e.g., Javaherian, K. et al. (1989) Proc. Natl. Acad. Sci. USA 86:6786-6772; Matsushita, M. et al. (1988) J. Virol. 62:2107-2144; Putney, S. et al. (1986) Science 234: 1392-1395; Rushe, J. R. et al. (1988) Proc. Nat. Acad. Sci. USA 85: 3198-3202; Matthews, T. (1986) Proc. Natl. Acad. Sci. USA. 83:9709-9713; Nara, P. L. et al. (1988) J. Virol. 62:2622-2628; Palker, T. J. et al. (1988) Proc. Natl. Acad. Sci. USA. 85:1932-1936).

Furthermore, although neutralizing antibodies are typically generated in the course of HIV infection in humans, that these antibodies do not provide permanent antiviral effect may in part be due to the generation of "neutralization escapes" virus mutants and to the general decline in the host immune system associated with pathogenesis. See, e.g., Barre-Sinoussi, F. et al. (1983) Science 220:868-871; Robert-Guroff, M. et al. (1985) Nature (London) 316:72-74; Weis, R. et al. (1985) Nature (London) 316:69-72; Weis, R. et al. (1986) Nature (London) 324:572-575. Nonetheless, it is widely believed that the presence of pre-existing neutralizing antibodies upon initial HIV-1 exposure will likely have a protective effect, for instance by attaching to the incoming virions and reducing or preventing their infectivity for target cells and prevent the cell-to-cell spread of virus in vivo. See, e.g., Hu et al. (1992) Science 255:456-459; Burton, D. R. and Montefiori, D. (1997) AIDS 11(suppl. A): 587-598; Montefiori and Evans (1999) AIDS Res. Hum. Ret. 15(8):689-698; Bolognesi, D. P. et al. (1994) Ann. Int. Med. 8:603-611; Haynes, B. F. et al. (1996) Science 271:324-328.

Several categories of potentially effective neutralizing antibodies have been identified. For example, in most infected individuals, a subset of broadly reactive antibodies that interfere with binding of gp120 and CD4 have been identified. See, e.g., Kang, C.-Y. et al. (1991) Proc. Natl. Acad. Sci. USA. 88:6171-6175; McDougal, J. S. et al. (1986) J. Immunol. 137:2937-2944. Monoclonal antibodies, such as IgG1b12, 2G12 (Mo et al. (1997) J. Virol 71:6869-6874), PA14 (Trkola et al. (2001) J. Virol. 75(2):579-588) and 2F5 also exhibit neutralizing effects. See, also, Trkola et al. (1995) J. Virol. 69:6609-6617; D'Sousa et al (1997) J. Infect. Dis. 175:1062-1075. Other antibodies are believed to bind to the chemokine receptor-binding region after CD4 has bound to Env (see, e.g., Thali et al. (1993) J. Virol. 67:3978-3988). Furthermore, in order to generate antibodies against the CD4 binding site region, which is exposed only upon binding to CD4, several groups have attempted to generate neutralizing antibodies by administering complexes of Env bound to CD4 (e.g., soluble CD4, referred to as "sCD4") or to CD4 mimetics (e.g., CD4M33). See, e.g., Martin et al. (2003) Nat. Biotechnol. 21(1):71-76.

In addition, WO 04/037847 describes Env-CD4 complexes useful in generating immune responses. Env-CD4 (sCD4) complexes are capable of inducing broadly neutralizing antibodies presumably by targeting conformational epitopes exposed in Env protein upon binding to CD4. However, if sCD4 is administered with an adjuvant, the potential for an autoimmune response is of serious concern. In addition, WO 04/037847 describes hybrid Env-CD4 polypeptides.

Despite the above approaches, there remains a need for additional molecules that can elicit an immunological response (e.g., neutralizing and/or protective antibodies) in a subject against multiple HIV strains and subtypes, for example when administered as a vaccine. The present invention solves these and other problems by providing immunogenic compositions comprising an HIV Tat polypeptide and a CD4 molecule as a unimolecular complex that also comprises an HIV Env polypeptide or as one part of a bimolecular complex comprising an HIV Tat/CD4 mini-protein portion and an Env portion.

SUMMARY

The present invention solves these and other problems by providing hybrid molecules comprising a CD4 polypeptide or CD4-like molecule and a scaffold polypeptide. In a preferred embodiment, the scaffold polypeptide is an Invasin polypeptide or fragment thereof. In another preferred embodiment, the scaffold polypeptide is a Tat polypeptide or fragment thereof. Preferably, an immune response to the Env-binding components (e.g., CD4 molecule) is not generated. However, the hybrid molecule binds to Env such that a conformational change in Env is induced and Env epitopes are exposed to which neutralizing antibodies are more readily generated. Thus, the hybrid molecules described herein allow for the production of useful antibodies against CD4-Env (including neutralizing antibodies and other immune responses), while reducing or eliminating unwanted immune responses to non-Env binding regions of CD4. Also provided are complexes of Env with the hybrid molecules described herein, as well as antibodies directed against these molecules.

Thus, in one aspect, the invention includes a hybrid comprising a CD4 protein or CD4 mimetic and a polypeptide derived from an HIV Tat protein. In certain embodiments, the CD4 protein comprises a CD4 minimal module and the Tat protein comprises a polypeptide derived from one or more full-length Tat proteins. In other embodiments, the Tat polypeptide comprises a fragment of an HIV-1 Tat protein (e.g., an 86 amino acid fragment of any HIV-1 Tat protein). The CD4 minimal module is preferably a human CD4 sequence. In certain embodiments, the hybrid molecule further comprises one or more additional polypeptides, for example immunomodulatory polypeptides (cytokines, etc.), and/or one or more Env polypeptides.

In another aspect, the invention includes complexes of the hybrid molecules described herein and an HIV Env polypeptide. Preferably, the complexes are formed such that cryptic epitopes are exposed in the Env polypeptide. The HIV Env polypeptide and hybrid molecules can be complexed by crosslinking (e.g., using formaldehyde); using a fixative (e.g., formalin); and/or can complex spontaneously under suitable conditions.

In another aspect, the invention includes a polynucleotide encoding one or more portions of the hybrid molecules described herein (e.g., operably linked CD4-encoding and Tat-encoding polynucleotide sequences). The polynucleotides encoding the CD4 polypeptides may be contiguous or non-contiguous and, in addition, may be 5', 3' and/or internal to (embedded within) one or more sequences encoding the Tat polypeptide(s). The Env polypeptide may also be provided as part of an immunogenic composition in the form of a polynucleotide encoding said Env polypeptide.

In some preferred embodiments, polynucleotides of the invention are modified (e.g., codon optimized) to increase expression in mammalian cells in vivo (for administration of polynucleic acids of the invention) or in vitro (for production of polypeptides of the invention).

Optionally, additional sequences can be included in the fusion proteins described herein. Further, when any of the polynucleotides described herein are expressed, the hybrid fusion protein preferably complexes with an HIV Env polypeptide such that cryptic epitopes are exposed in the Env polypeptide.

In yet another aspect, the invention includes immunogenic compositions comprising any of the molecules (e.g., polynucleotides and/or polypeptides) described herein. In certain embodiments, the immunogenic compositions further comprise one or more adjuvants.

In a still further aspect, the invention includes a cell comprising any of the molecules (e.g., polynucleotides and/or polypeptides) described herein. When used as polynucleotides, the sequences are preferably operably linked to control elements compatible with expression in the selected cell. The cell can be, for example, a mammalian cell (e.g., BHK, VERO, HT1080, 293, RD, COS-7, and CHO cells); an insect cell (e.g., Trichoplusia ni (Tn5) or Sf9 cells); a bacterial cell; a yeast cell; a plant cell; an antigen presenting cell; a lymphoid cell selected from the group consisting of macrophage, monocytes, dendritic cells, B-cells, T-cells, stem cells, and progenitor cells thereof; a primary cell; an immortalized cell; and/or a tumor-derived cell.

In another aspect, the invention includes a vector for use in a mammalian subject, wherein the vector comprises any of the polynucleotides described herein operably linked to control elements compatible with expression in the subject.

In yet another aspect, the invention includes a method of producing antibodies that bind to cryptic epitopes of HIV Env, the method comprising the step of administering any of the hybrid molecules (e.g., fusion proteins) described herein to a subject under conditions that allow production of antibodies (e.g., neutralizing antibodies, monoclonal antibodies, polyclonal antibodies) in the subject. In certain embodiments, the antibodies produced in the subject are then isolated.

In a still further aspect, the invention includes a method for producing any of the hybrid fusion proteins described herein, said method comprising incubating any of the cells described herein, under conditions suitable for producing said fusion protein.

In a still further aspect, the invention includes a method for producing complexes of any of the hybrid molecules described herein with HIV Env, the method comprising incubating a Tat-CD4 hybrid molecule as described herein (or polynucleotide encoding said molecule) under conditions suitable for producing a complex of the fusion protein with HIV Env.

In yet another aspect, the invention includes a method of inducing an immune response (e.g., a humoral response such as a neutralizing antibody response and/or a cellular immune response) in subject comprising, administering any of the molecules (e.g., polynucleotides, polypeptides and/or immunogenic compositions) described herein to a subject in an amount sufficient to induce an immune response (e.g., against cryptic Env epitopes) in the subject. In certain embodiments, the method comprises transfecting cells ex vivo and reintroducing the transfected cells into the subject. In other embodiments, the method includes DNA immunization of a subject, for example, by introducing any of the polynucleotides and/or vectors described herein into said subject under conditions that are compatible with expression of said expression cassette and production of a polypeptide in said subject. In other embodiments, the methods comprise (a) administering a first composition comprising any of the polynucleotides described herein in a priming step and (b) administering a second composition comprising any of the polypeptides described herein, as a booster, in an amount sufficient to induce an immune response in the subject. In any of the methods described herein, the vectors may comprise non-viral vectors or viral vectors such as retroviral (e.g., lentiviral) vectors. Further, the polynucleotides and/or vector may be introduced, for example, using a particulate carrier (e.g., coated on a gold or tungsten particle and said coated particle is delivered to said subject using a gene gun) or encapsulated in a liposome preparation. In any of the methods described herein, the subject can be a mammal, for example a human or non-human mammal and the introduction can be, for example, intramuscularly, intramucosally, intranasally, subcutaneously, intradermally, transdermally, intravaginally, intrarectally, orally and/or intravenously.

The following embodiments are encompassed by the present invention:

1. A hybrid molecule composition comprising a scaffold polypeptide and a CD4 mini-protein, wherein said hybrid molecule induces a conformational change in an HIV Env polypeptide when said hybrid molecule binds to said HIV Env polypeptide.

2. The composition of embodiment 1, wherein said scaffold polypeptide is selected from the group consisting of Invasin and tat polypeptides.

2A. The composition of embodiment 1 or 2, wherein said scaffold polypeptide is a heterologous polypeptide.

2B. The composition of embodiment 1 or 2, wherein said scaffold polypeptide is a homolgous polypeptide.

3. A hybrid molecule composition comprising an HIV Tat polypeptide or fragment thereof; and a CD4 mini-protein, wherein said hybrid molecule binds to an HIV Env polypeptide.

4. The composition of any one of embodiments 1 to 3, wherein the CD4 mini-protein is a CD4 minimal module comprising amino acid residues 15 to 85 of CD4.

5. The composition of any one of embodiments 1 to 3, wherein the Tat polypeptide comprises a full-length Tat polypeptide or variant thereof.

6. The composition of embodiment 5, wherein the Tat polypeptide is a fragment of a full-length Tat polypeptide or variant thereof comprising amino acid residues 1-86 of a Tat protein, numbered relative to SEQ ID NO:2 or a variant thereof.

7. The composition of any of one of embodiments 1 to 6 which further comprises one or more additional heterologous polypeptides.

8. The composition of embodiment 7, wherein the one or more additional heterologous polypeptides are selected from the group consisting of viral polypeptides, immunomodulatory polypeptides and bacterial polypeptides.

9. The composition of embodiment 8, wherein the additional heterologous polypeptide is a viral polypeptide and the virus is HIV.

10. The composition of any one of embodiments 1 to 9, wherein one or more of said HIV tat polypeptide or fragment thereof, CD4 mini-protein and additional heterologous polypeptides is provided as a polynucleotide encoding the polypeptide, fragment thereof or mini-protein.

11. An immunogenic composition comprising the composition of any one of embodiments 1 to 9 and further comprising an HIV Env polypeptide.

12. The immunogenic composition of embodiment 11 wherein the Env polypeptide comprises gp120.

13. The immunogenic composition of embodiment 11 wherein the Env polypeptide comprises oligomeric gp140.

14. The immunogenic composition of embodiment 11 wherein the composition of any of embodiments 1 to 10 and Env are complexed by cross-linking the composition of any of embodiments 1 to 10 to Env.

15. The immunogenic composition of embodiment 14 wherein the composition of any of embodiments 1 to 13 and Env are cross-linked using a fixative.

16. The immunogenic composition of embodiment 15, wherein the fixative comprises formaldehyde, 17. The immunogenic composition of embodiment 15, wherein the fixative comprises gluteraldehyde.

18. The immunogenic composition of embodiment 11, wherein the composition of any of embodiments 1 to 13 and the Env polypeptide spontaneously form a complex.

19. The immunogenic composition of embodiment 11, wherein the composition of any of embodiments 1 to 13 comprises a CD4 minimal module-Tat fusion protein.

20. The immunogenic composition according to embodiments 11 to 19, which further comprises an adjuvant.

21. A polynucleotide encoding at least one of an HIV tat polypeptide or fragment thereof, CD4 mini-protein and an additional heterologous polypeptide.

22. The polynucleotides of embodiment 21 which further encodes an Env polypeptide.

23. A cell comprising the polynucleotide of embodiment 21 or embodiment 22, and wherein said polynucleotide is operably linked to control elements compatible with expression in the selected cell.

24. The cell of embodiment 23, wherein the cell is a mammalian cell.

25. The cell of embodiment 23, wherein the cell is selected from the group consisting of BHK, VERO, HT1080, 293, RD, COS-7, and CHO cells.

26. The cell of embodiment 24, wherein said cell is a CHO cell.

27. The cell of embodiment 23, wherein the cell is an insect cell.

28. The cell of embodiment 27, wherein the cell is either *Trichoplusia ni* (Tn5) or Sf9 insect cells.

29. The cell of embodiment 23, wherein the cell is a bacterial cell.

30. The cell of embodiment 23, wherein the cell is a yeast cell.

31. The cell of embodiment 23, wherein the cell is a plant cell.

32. The cell of embodiment 23, wherein the cell is an antigen presenting cell.

33. The cell of embodiment 23, wherein the cell is a lymphoid cell selected from the group consisting of macrophage, monocytes, dendritic cells, B-cells, T-cells, stem cells, and progenitor cells thereof.

34. The cell of embodiment 23, wherein the cell is a primary cell.

35. The cell of embodiment 23, wherein the cell is an immortalized cell.

36. The cell of embodiment 23, wherein the cell is a tumor-derived cell.

37. A gene delivery vector for use in a mammalian subject, comprising a suitable gene delivery vector for use in said subject, wherein the vector comprises a polynucleotide according to embodiment 21 or embodiment 22, and wherein said polynucleotide is operably linked to control elements compatible with expression of the polynucleotide in the subject.

38. A method of producing antibodies that bind to functional epitopes of HIV Env, the method comprising the step of: administering an immunogenic composition according to any one of embodiments 11 to 20 to a subject under conditions that allow production of antibodies in the subject.

39. The method of embodiment 38, further comprising the step of isolating the antibodies produced in the subject.

40. The method of embodiment 38 or embodiment 39, wherein the antibodies are neutralizing antibodies.

41. The method of embodiment 38 or 39, wherein the antibodies elicit ADCC activity.

42. The method of any one of embodiment 38 to 41, wherein the antibodies are monoclonal antibodies.

43. The method of any one of embodiment 38 to 42, wherein the antibodies are polyclonal antibodies.

44. A method for producing a polypeptide comprising an HIV Env polypeptide sequence complexed to CD4 proteins, said method comprising incubating the cells of any of embodiments 23 to 36 under conditions for producing said polypeptide.

45. A method of inducing an immune response in subject comprising, administering a composition according to any one of embodiments 11 to 20 in an amount sufficient to induce an immune response in the subject.

46. A method of DNA immunization of a subject, comprising, introducing a gene delivery vector of embodiment 37 into said subject under conditions that are compatible with expression of said expression cassette in said subject.

47. The method of embodiment 46, wherein said gene delivery vector is a nonviral vector.

48. The method of embodiment 46, wherein said vector is delivered using a particulate carrier.

49. The method of embodiment 48, wherein said vector is coated on a gold or tungsten particle and said coated particle is delivered to said subject using a gene gun.

50. The method of embodiment 46, wherein said vector is encapsulated in a liposome preparation.

51. The method of embodiment 46, wherein said vector is a viral vector.

52. The method of embodiment 51, wherein said viral vector is a retroviral vector.

53. The method of embodiment 51, wherein said viral vector is a lentiviral vector.

54. The method of embodiment 46, wherein said subject is a mammal.

55. The method of embodiment 54, wherein said mammal is a human.

56. A method of generating an immune response in a subject, comprising transfecting cells of said subject with a gene delivery vector of embodiment 37, under conditions that permit the expression of said polynucleotide and production of said polypeptide, thereby eliciting an immunological response to said polypeptide.

57. The method of embodiment 56, wherein said vector is a nonviral vector.

58. The method of embodiment 57, wherein said vector is delivered using a particulate carrier.

59. The method of embodiment 58, wherein said vector is coated on a gold or tungsten particle and said coated particle is delivered to said vertebrate cell using a gene gun.

60. The method of embodiment 59, wherein said vector is encapsulated in a liposome preparation.

61. The method of embodiment 56, wherein said vector is a viral vector.

62. The method of embodiment 61, wherein said viral vector is a retroviral vector.

63. The method of embodiment 62, wherein said viral vector is a lentiviral vector.

64. The method of embodiment 56, wherein said subject is a mammal.

65. The method of embodiment 64, wherein said mammal is a human.

66. The method of embodiment 56, wherein said transfecting is done ex vivo and said transfected cells are reintroduced into said subject.

67. The method of embodiment 56, wherein said transfecting is done in vivo in said subject.

68. The method of embodiment 56, where said immune response is a humoral immune response.

69. The method of embodiment 56, where said immune response is a cellular immune response.

70. The method of any one of embodiment 56 to 69, wherein the gene delivery vector is administered intramuscularly, intramucosally, intranasally, subcutaneously, intradermally, transdermally, intravaginally, intrarectally, orally or intravenously.

71. A method of inducing an immune response in a subject comprising
    (a) administering a first composition, wherein said first composition comprises a polynucleotide according to embodiment 21 or 22 in a priming step and
    (b) administering a second composition as a booster, in an amount sufficient to induce an immune response in the subject, wherein said second composition comprises a composition according to any one of embodiment 1 to 20.

72. The method of embodiment 71, wherein the first composition or second composition further comprises an adjuvant.

73. The method of embodiment 71, wherein the first composition further comprises a sequence encoding an HIV Gag polypeptide.

74. The method of embodiment 71, wherein the second composition further comprises an HIV Gag polypeptide.

These and other embodiments of the subject invention will readily occur to those of skill in the art in light of the disclosure herein.

BRIEF DESCRIPTION OF THE DRAWINGS

FIG. 1 depicts the primary amino acid sequence of a human CD4 protein (GenBank Accession No. NP_000607) (SEQ ID NO: 1).

FIG. 2 depicts the primary amino acid sequence of an exemplary HIV-1 Tat protein from subtype B strain HXB2 (SEQ ID NO: 2).

FIG. 3 depicts the primary amino acid sequence of another exemplary HIV-1 Tat protein from SF162 (SEQ ID NO: 3).

FIG. 5 shows schematics depicting exemplary CD4 minimal module-Tat hybrid molecules described herein. The first CD4 minimal module Tat hybrid molecule depicted comprises, in the N-terminal to C-terminal direction, residues 1-20 of a Tat protein, residues 15-85 of CD4 (SEQ ID NO: 1) (CD4 minimal module); and residues 30-86 of a Tat protein. The second hybrid molecule depicted comprises, in the N-terminal to C-terminal direction, residues 1-30 of a Tat protein, residues 15-85 of CD4 (SEQ ID NO: 1) (CD4 minimal module); and residues 40-86 of a Tat protein. The third hybrid molecule depicted comprises, in the N-terminal to C-terminal direction, residues 1-40 of a Tat protein, residues 15-85 of CD4 (SEQ ID NO: 1) (CD4 minimal module); and residues 50-86 of a Tat protein. The fourth hybrid molecule depicted comprises, in the N-terminal to C-terminal direction, residues 1-50 of a Tat protein, residues 15-85 of CD4 (SEQ ID NO: 1) (CD4 minimal module); and residues 60-86 of a Tat protein.

FIG. 6 depicts amino acid sequences of 4 exemplary CD4 minimal module-Tat hybrid molecules. The Tat component of these hybrid molecules is derived from an HIV bru isolate. The first amino acid sequence (SEQ ID NO: 4) depicted is for a hybrid molecule comprising, in the N-terminal to C-terminal direction, residues 1-20 of a Tat protein, residues 15-85 of CD4 (SEQ ID NO: 1) (CD4 minimal module); and residues 30-86 of a Tat protein. The second amino acid sequence (SEQ ID NO: 5) depicted is for a hybrid molecule comprising, in the N-terminal to C-terminal direction, residues 1-30 of a Tat protein, residues 15-85 of CD4 (SEQ ID NO: 1) (CD4 minimal module); and residues 40-86 of a Tat protein. The third amino acid sequence (SEQ ID NO: 6) depicted is for a hybrid molecule comprising, in the N-terminal to C-terminal direction, residues 1-40 of a Tat protein, residues 15-85 of CD4 (SEQ ID NO: 1) (CD4 minimal module); and residues 50-86 of a Tat protein. The fourth amino acid sequence (SEQ ID NO: 7) depicted is for a hybrid molecule comprising, in the N-terminal to C-terminal direction, residues 1-50 of a Tat protein, residues 15-85 of CD4 (SEQ ID NO: 1) (CD4 minimal module); and residues 60-86 of a Tat protein.

FIG. 7 depicts amino acid sequences of 4 exemplary CD4 minimal module-Tat hybrid molecules. The Tat component of these hybrid molecules is derived from an HIV SF162 isolate. The first amino acid sequence (SEQ ID NO: 8) depicted is for a hybrid molecule comprising, in the N-terminal to C-terminal direction, residues 1-20 of a Tat protein, residues 15-85 of CD4 (SEQ ID NO: 1) (CD4 minimal module); and residues 30-86 of a Tat protein. The second amino acid sequence (SEQ ID NO: 9) depicted is for a hybrid molecule comprising, in the N-terminal to C-terminal direction, residues 1-30 of a Tat protein, residues 15-85 of CD4 (SEQ ID NO: 1) (CD4 minimal module); and residues 40-86 of a Tat protein. The third amino acid sequence (SEQ ID NO: 10) depicted is for a hybrid molecule comprising, in the N-terminal to C-terminal direction, residues 1-40 of a Tat protein, residues 15-85 of CD4 (SEQ ID NO: 1) (CD4 minimal module); and residues 50-86 of a Tat protein. The fourth amino acid sequence (SEQ ID NO: 11) depicted is for a hybrid molecule comprising, in the N-terminal to C-terminal direction, residues 1-50 of a Tat protein, residues 15-85 of CD4 (SEQ ID NO: 1) (CD4 minimal module); and residues 60-86 of a Tat protein.

FIG. 8 depicts an alignment of the amino acid sequence (SEQ ID NO: 12) for a Tat protein from an HIV bru isolate and the amino acid sequence (SEQ ID NO: 13) for a Tat protein from an HIV SF162 isolate.

DETAILED DESCRIPTION

Figure 4:
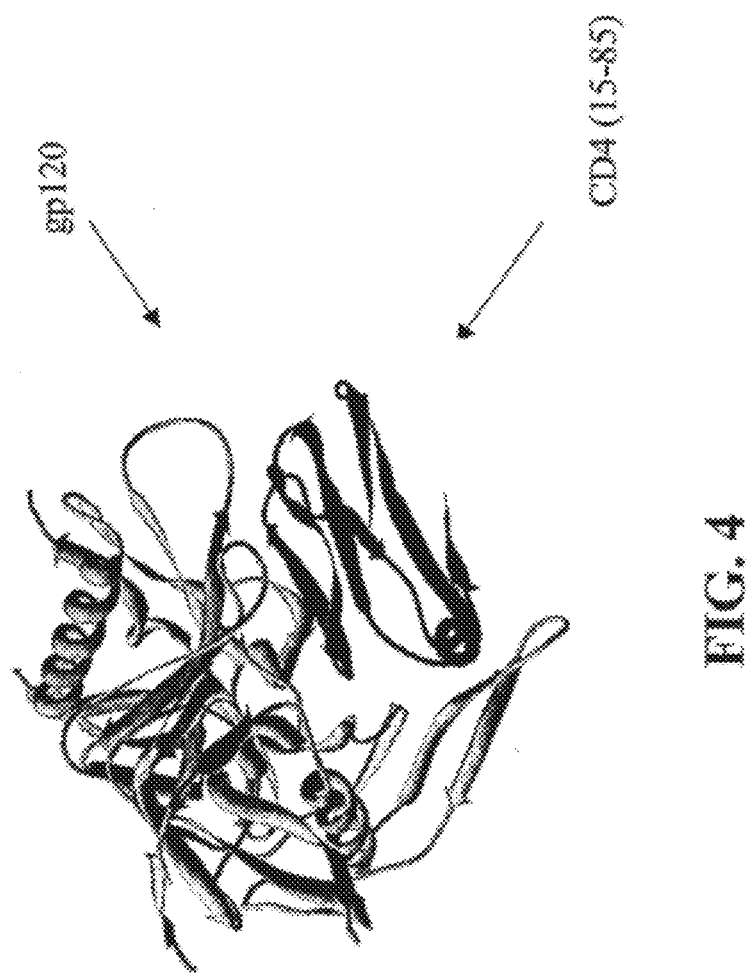
FIG. 4 is a schematic diagram depicting a CD4 mini-protein involved in env binding. The CD4 minimal module (darker gray) corresponds to residues 15-85 of SEQ ID NO:1 and is structurally stabilized by the presence of a disulfide bridge between Cys16 and Cys84.

The practice of the present invention will employ, unless otherwise indicated, conventional methods of protein chemistry, viral immunobiology, molecular biology and recombinant DNA techniques within the skill of the art. Such techniques are explained fully in the literature. See, e.g., T. E. Creighton, *Proteins: Structures and Molecular Properties* (W.H. Freeman and Company, 1993); Nelson L. M. and Jerome H. K. *HIV Protocols in Methods in Molecular Medicine*, vol. 17, 1999; Sambrook et al., *Molecular Cloning: A Laboratory Manual* (Cold Spring Harbor Laboratory, 1989); F. M. Ausubel et al. *Current Protocols in Molecular Biology*, Greene Publishing Associates & Wiley Interscience New York; and Lipkowitz and Boyd, Reviews in Computational Chemistry, volumes 1-present (Wiley-VCH, New York, N.Y., 1999).

It must be noted that, as used in this specification and the appended embodiments, the singular forms "a", "an" and "the" include plural referents unless the content clearly dictates otherwise. Thus, for example, reference to "a polypeptide" includes a mixture of two or more polypeptides, and the like.

All publications, patents and patent applications cited herein, whether supra or infra, are hereby incorporated by reference in their entirety.

Definitions

In describing the present invention, the following terms will be employed, and are intended to be defined as indicated below.

The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include post expression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents that will find use in the present invention are set forth below.

By "geometry," "architecture," or "tertiary structure" of a polypeptide or protein is meant the overall 3-D configuration of the protein. As described herein, the geometry can be determined, for example, by crystallography studies or by using various programs or algorithms that predict the geometry based on interactions between the amino acids making up the primary and secondary structures.

By "wild type" or "native" polypeptide, polypeptide agent or polypeptide drug, is meant a naturally occurring polypeptide sequence, and its corresponding secondary structure. An "isolated" or "purified" protein or polypeptide is a protein that is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

The terms "CD4 mini-protein," "CD4 minimal module," "CD4 mimetic" and "mini CD4 protein" are used interchangeably to refer to any molecule that interacts with env, preferably such that functional epitopes (e.g., cryptic epitopes) in or near the CD4 and/or chemokine receptor or other critical binding sites(s) are exposed. Thus, a CD miniprotein can be a less than full-length fragment of CD4 including truncations and deletions. In addition, the term encompasses functional and structural homologs of CD4 fragments, i.e., polypeptides that expose the cryptic epitopes on an Env protein. The amino acid sequence for human CD4 is incorporated herein from Maddon et al. (1985) *Cell* 42:93; and Littman et al. (1988) *Cell* 55:541) and shown as FIG. 1 (SEQ ID NO:1). In addition, the term encompasses functional and structural homologs of CD4 fragments, i.e., mimetics and/or polypeptides that expose the cryptic epitopes on an Env protein. See, e.g., Martin et al. (2003) *Nat Biotechnol.* 21(1):71-6; Vita et al. (1998) *Biopolymers* 47(1):93-100; Vita et al. (1999) *Proc Natl Acad Sci USA* 96(23):13091-13096.

A "scaffold polypeptide" as used herein comprises a polypeptide that presents the minimal CD4 molecule to Env in an overall configuration that mimics the conformational changes seen when native CD4 binds to env. In this way, the binding of the CD4 minimal module-containing hybrid molecule to Env is enhanced while reducing unwanted immune responses to non-Env binding regions of CD4. In addition to providing a CD4-like structure (or scaffold) the scaffold polypeptide may also impart other functions to the hybrid molecules described herein. Other functions of the scaffold component include, but are not limited to, immunogenicity, adjuvanticity and/or immunomodulatory characteristics. Proteins exhibiting structural similarity to native CD4 may be identified by performing searches of structural databases, using methods known to those of skill in the art and as described herein. See, also, International Application No. PCT/US05/022801. Scaffold polypeptides can be homologous (containing sequences from a single polypeptide) or heterologous (containing sequences from more than one polypeptide). Scaffold polypeptides can comprise contiguous or non-contiguous, naturally occurring or artificial sequences, so long as the hybrid molecule(s) into which they are incorporated retain the function of inducing a conformational change in env when the hybrid molecule is bound to env, thereby exposing functional epitopes for inducing, e.g., neutralizing antibodies that prevent or limit HIV infection.

By "Tat polypeptide" is meant a molecule derived from a viral transactivation (Tat) protein, preferably from HIV Tat. HIV Tat proteins are small proteins, typically between about 86-101 residues in length, and have been shown to have a number of effects on HIV-infected and uninfected cells. See, e.g., Opi et al. (2002) *J. Biol. Chem.* 277(39):35915-35919. Tat proteins include two functional regions, a cysteine-rich (from about amino acid20 to amino acid 31) region and a basic (from about amino acid 48 to amino acid 47) region. See, e.g., Jeang et al. (1999) *J. Biol. Chem.* 274:28837-28840. It will be apparent to those working in the field that Tat proteins from different strains may vary in overall length and in particular residues as compared to the exemplary Tat sequences shown in SEQ ID NOs:2 and 3. Any Tat protein from any isolate can be readily aligned with the sequences presented herein and known in the art to determine corresponding residues. As used herein, a tat polypeptide includes deletions, truncations and other variants, both artificial and naturally occurring, of tat as discussed herein. The Tat polypeptide portion(s) of the hybrid molecules can be selected for any number of characteristics including, their ability to act as scaffold, thereby presenting the CD4 molecules to Env in an overall configuration that mimics CD4, regardless of the length of the Tat polypeptide utilized.

By "Env polypeptide" is meant a molecule derived from an envelope protein, preferably from HIV Env. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

By a "gp120 polypeptide" is meant a molecule derived from a gp120 region of the Env polypeptide. Preferably, the gp120 polypeptide is derived from HIV Env. The primary amino acid sequence of gp120 is approximately 511 amino acids, with a polypeptide core of about 60,000 Daltons. The polypeptide is extensively modified by N-linked glycosylation to increase the apparent molecular weight of the molecule to 120,000 Daltons. The amino acid sequence of gp120 contains five relatively conserved domains interspersed with five hypervariable domains. The positions of the 18 cysteine residues in the gp120 primary sequence of the HIV-1$_{HXB-2}$ (hereinafter "HXB-2") strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 polypeptide" includes both single subunits and/or multimers.

Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 119 (Cys) to amino acid residue 123 (Thr) while β-3 occurs at approximately amino acid residue 199 (Ser) to amino acid residue 201 (Ile), relative to HXB-2. The "V1/V2 region" occurs at approximately amino acid positions 126 (Cys) to residue 196 (Cys), relative to HXB-2 (see, e.g., Wyatt et al. (1995) *J. Virol.* 69:5723-5733; Stamatatos et al. (1998) *J. Virol.* 72:7840-7845). Extruding from the second pair of β-strands (β-20 and β-21) is a "small-loop" structure, also referred to herein as "the bridging sheet small loop." In HXB-2, β-20 extends from about amino acid residue 422 (Gln) to amino acid residue 426 (Met) while β-21 extends from about amino acid residue 430 (Val) to amino acid residue 435 (Tyr). In variant SF162, the Met-426 is an Arg (R) residue. The "small loop" extends from about amino acid residue 427 (Trp) through 429 (Lys), relative to HXB-2. Alignment of the amino acid sequences of Env polypeptide gp160 of any HIV variant can be determined relative to other variants, such as HXB-2, as described for example, in WO 00/39303.

Furthermore, an "Env polypeptide," "gp120 polypeptide" or "Tat polypeptide" as defined herein is not limited to a polypeptide having the exact sequence described herein. Indeed, the HIV genome is in a state of constant flux and contains several variable domains that exhibit relatively high degrees of variability between isolates. It is readily apparent that the terms encompass Env (e.g., gp120) and tat polypeptides from any of the identified HIV isolates, as well as newly identified isolates, and subtypes of these isolates. Descriptions of structural features are given herein with reference to HXB-2 unless otherwise indicated. One of ordinary skill in the art in view of the teachings of the present disclosure and the art can determine corresponding regions in other HIV variants (e.g., isolates HIV$_{IIIb}$, HIV$_{SF2}$, HIV-1$_{SF162}$, HIV-1$_{SF170}$, HIV$_{LAV}$, HIV$_{LAI}$, HIV$_{MN}$, HIV-1$_{CM235}$, HIV-1$_{US4}$, other HIV-1 strains from diverse subtypes (e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., *Virology,* 3rd Edition (W. K. Joklik ed. 1988); *Fundamental Virology,* 2nd Edition (B. N. Fields and D. M. Knipe, eds. 1991); *Virology,* 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the polypeptides described herein can be based on any HIV variant.

Additionally, the terms "Env polypeptide" (e.g., "gp120 polypeptide") and "Tat polypeptide" encompass proteins that include additional modifications to the native sequence, such as additional internal deletions, additions, truncations and substitutions. These modifications may be deliberate, as through site-directed mutagenesis, or may be accidental, such as through naturally occurring mutational events. Thus, for example, if modifications are made to an Env polypeptide is to be used in vaccine compositions, the modifications are preferably such that immunological activity (i.e., the ability to elicit an antibody response to the polypeptide) is not lost. Similarly, if the polypeptides are to be used for diagnostic purposes, such capability must be retained.

A "modified Env polypeptide" is an Env polypeptide (e.g., gp120 as defined above), which has been complexed to a fusion protein comprising a CD4 minimal module as described herein. The Env polypeptide may be monomeric or oligomeric. Generally, complexed Env (e.g., gp120) polypeptides result in exposure of epitopes in or near the CD4 binding site, while allowing correct folding (e.g., correct geometry) of the Env polypeptide. Additionally, modifications (e.g., truncations) to the V1 and V2 loop regions may also be made. Although not all possible V1/V2 modifications have been exemplified herein, it is to be understood that other disrupting modifications are also encompassed by the present invention.

The terms "hybrid molecule" and "fusion molecule" refers to a molecule in which two or more subunit molecules are linked, either covalently or non-covalently. The subunit molecules can be the same chemical type of molecule, or can be different chemical types of molecules. Thus, as used herein, the term refers to any molecule containing CD4 mini proteins and at least one Tat polypeptide. Fusion molecules include, but are not limited to, fusion polypeptides (for example, a fusion between a CD4 polypeptide and a non-CD4 polypeptide) and fusion nucleic acids (for example, a nucleic acid encoding the fusion polypeptide). When used in reference to proteins comprising one or more CD4 minimal modules, the terms "fusion protein" or "fusion polypeptide" refer to polypeptides in which CD4 amino acid sequences (e.g., Env-binding sequences) and one or more heterologous (non-CD4) polypeptides are expressed in a single protein. The CD4 polypeptide(s) may be flanked on one or both sides by the Tat polypeptide(s). A wild-type HIV Tat amino acid sequence is shown in FIG. 2 (SEQ ID NO:2). See, also, Ratner et al. (1985) *Nature* 313:277-284. Non-limiting examples of fragments of Tat useful in constructing fusion proteins as described herein include a region extending from about amino acid residues 1-86, numbered relative to SEQ ID NO:2. See, also, GenBank Accession No. P04606.

By "binding" is meant the ability of a hybrid molecule to specifically interact with an Env polypeptide such that interaction results in a conformational change in the Env polypeptide that leads to exposure of Env epitopes to which neutralizing antibodies are more readily generated.

Normally, fusion proteins are capable of secretion into growth medium in which an organism expressing the protein is cultured. However, for purposes of the present invention, such polypeptides may also be recovered intracellularly. Secretion into growth media is readily determined using a number of detection techniques, including, e.g., polyacrylamide gel electrophoresis and the like, and immunological techniques such as Western blotting and immunoprecipitation assays as described in, e.g., International Publication No. WO 96/04301.

A polypeptide (e.g., gp120 or other Env polypeptide) is produced "intracellularly" when it is found within the cell, either associated with components of the cell, such as in association with the endoplasmic reticulum (ER) or the Golgi Apparatus, or when it is present in the soluble cellular fraction. The polypeptides of the present invention may also be secreted into growth medium so long as sufficient amounts of the polypeptides remain present within the cell such that they can be purified from cell lysates using techniques described herein.

An "immunogenic molecule" or "immunogenic composition" refers to a molecule that includes at least one epitope such that the molecule is capable of either eliciting an immunological reaction in an individual to which the protein is administered or, in the diagnostic context, is capable of reacting with antibodies directed against the HIV in question.

By "epitope" is meant a site on an antigen to which specific B cells and/or T cells respond, rendering the molecule including such an epitope capable of eliciting an immunological reaction or capable of reacting with HIV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen. A "cryptic epitope" refers generally to an epitope that is exposed only in certain conformations of the protein.

A "functional epitope" refers to an epitope that elicits antibody which prevents or limits HIV infection. In a preferred embodiment, the antibodies are neutralizing antibodies. In other embodiments, the antibodies can, e.g. elicit an ADCC response.

An "immunological response" or "immune response" as used herein can include the development in the subject of a humoral and/or a cellular immune response to the Env (e.g., gp120) polypeptide when the polypeptide is present in a vaccine composition. Antibodies elicited in an immune response may also neutralize infectivity, and/or mediate antibody-complement or antibody dependent cell cytotoxicity to provide protection to an immunized host. Immunological reactivity may be determined in standard immunoassays, such as a competition assays, well known in the art.

The term "antibody" as used herein includes antibodies obtained from both polyclonal and monoclonal preparations, as well as, the following: (i) hybrid (chimeric) antibody molecules (see, for example, Winter et al. (1991) *Nature* 349:293-299; and U.S. Pat. No. 4,816,567); (ii) F(ab')2 and F(ab) fragments; (iii) Fv molecules (noncovalent heterodimers, see, for example, Inbar et al. (1972) *Proc. Natl. Acad. Sci. USA* 69:2659-2662; and Ehrlich et al. (1980) Biochem 19:4091-4096); (iv) single-chain Fv molecules (sFv) (see, for example, Huston et al. (1988) *Proc. Natl. Acad. Sci. USA* 85:5879-5883); (v) dimeric and trimeric antibody fragment constructs; (vi) humanized antibody molecules (see, for example, Riechmann et al. (1988) *Nature* 332:323-327; Verhoeyan et al. (1988) *Science* 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) *Biochem* 31:1579-1584; Cumber et al. (1992) *J. Immunology* 149B:120-126); and, (vii) any functional fragments obtained from such molecules, wherein such fragments retain specific-binding properties of the parent antibody molecule.

Thus, the term "antibody" refers to a polypeptide or group of polypeptides that comprise at least one antigen binding site. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen binding site may be formed from a heavy- and/or light-chain domain (VH and VL, respectively), which form hypervariable loops that contribute to antigen binding. The term "antibody" includes, without limitation, polyclonal antibodies, monoclonal antibodies, chimeric antibodies, altered antibodies, univalent antibodies, Fab proteins, and single-domain antibodies. In many cases, the binding phenomena of antibodies to antigens is equivalent to other ligand/anti-ligand binding.

If polyclonal antibodies are desired, a selected mammal (e.g., mouse, rabbit, goat, horse, etc.) is immunized with an immunogenic polypeptide bearing an HCV epitope(s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker, eds. (1987) *Immunochemical Methods In Cell And Molecular Biology* (Academic Press, London).

One skilled in the art can also readily produce monoclonal antibodies directed against HCV epitopes. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) *Hybridoma Techniques*; Hammerling et al. (1981), *Monoclonal Antibodies and T-Cell Hybridomas*; Kennett et al. (1980) *Monoclonal Antibodies*; see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc. As used herein, a "single domain antibody" (dAb) is an antibody that is comprised of an HL domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al. (1989) *Nature* 341: 544.

Antibodies can also be comprised of $V_H$ and $V_L$ domains, as well as other known antigen binding domains. Examples of these types of antibodies and methods for their preparation and known in the art (see, e.g., U.S. Pat. No. 4,816,467, which is incorporated herein by reference), and include the following. For example, "vertebrate antibodies" refers to antibodies that are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation, See, e.g., Glennie at al. (1982) *Nature* 295: 712. Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)2), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers town exact nucleotide to nucleotide or amino acid to amino acid correspondence of two polynucleotides or polypeptide sequences, respectively.

Two or more polynucleotide sequences can be compared by determining their "percent identity". Two or more amino acid sequences likewise can be compared by determining their "percent identity". The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* (1981) 2:482-489. This algorithm can be extended to use with peptide sequences using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov (1986) *Nucl. Acids Res.* 14(6): 6745-6763. An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and embodiments), including all integer values falling within the above-described ranges.

Generally, the polypeptides and/or polynucleotides of the present invention can or may include related sequences having about 80% to 100%, greater than 80-85%, preferably greater than 90-92%, more preferably greater than 95%, and most preferably greater than 98% sequence (including all integer values falling within these described ranges) identity to the molecules described herein (for example, to the disclosed sequences or other sequences of the present invention) when the sequences of the present invention are used as the query sequence.

Computer programs are also available to determine the likelihood of certain polypeptides to form structures such as β-sheets. One such program, described herein, is the "ALB" program for protein and polypeptide secondary structure calculation and predication. In addition, secondary protein structure can be predicted from the primary amino acid sequence, for example using protein crystal structure and aligning the protein sequence related to the crystal structure (e.g., using Molecular Operating Environment (MOE) programs available from the Chemical Computing Group Inc., Montreal, P.Q., Canada). Other methods of predicting secondary structures are described, for example, in Garnier et al. (1996) *Methods Enzymol.* 266:540-553; Geourjon et al. (1995) *Comput. Applic. Biosci,* 11:681-684; Levin (1997) *Protein Eng.* 10:771-776; and Rost et al. (1993) *J. Molec. Biol.* 232:584-599.

Homology can also be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences may exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* supra; *Nucleic Acid Hybridization,* supra.

A "coding sequence" or a sequence that "encodes" a selected protein, is a nucleic acid sequence that is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic and semisynthetic DNA sequences and sequences including base analogs. A transcription termination sequence may be located 3' to the coding sequence.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they function to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used inter-changeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to fluorescein, rhodamine, dansyl, umbelliferone, Texas red, luminol, acradimum esters, NADPH, beta-galactosidase, horseradish peroxidase, glucose oxidase, alkaline phosphatase and urease.

Overview

The present invention relates to fusion molecules comprising CD4 proteins and/or CD4 mimetics and Tat proteins, complexes of these molecules with HIV Env polypeptides, as well as methods of making and using these molecules and complexes. Without being bound by a particular theory, it appears that it has been difficult to generate immunological responses against Env because the CD4 binding site (and/or the CCR binding site) is buried between the outer domain, the inner domain and the V1/V2 domains of Env. Thus, although deletion of the V1/V2 domain may render the virus more susceptible to neutralization by monoclonal antibody directed to the CD4 site, the conformation of Env prior to CD4 binding may prevent an antibody response. Furthermore, when full length or near full length CD4 (e.g., soluble CD4 or sCD4) is used to induce the conformational change in Env, the immune system also mounts a response to the non-bound portions of CD4.

Thus, the present invention provides molecules comprising fragments or mimetics of CD4 in combination with Tat proteins. The CD4 component generally does not include regions to which CD4 immune response is generated while still including sequences involved in binding to the Env. Thus, the fusion molecules bind to Env without eliciting unwanted immune responses, for example to full-length CD4. Further, these fusion proteins cause a conformational change in Env that exposes one or more epitopes (e.g., cryptic epitopes) in or near the CD4 binding site, which in turn allows the generation of an immune response (e.g., a neutralizing antibody response) to Env without the unwanted immune response to CD4.

Various forms of the different embodiments of the invention, described herein, may be combined.

CD4 Molecules

In the practice of the present invention, hybrid molecules comprise CD4 molecules. The hybrid molecules may be complexed to Env polypeptides in order to change conformation of the Env polypeptide and expose epitopes that elicit neutralizing antibodies.

The amino acid sequence of CD4 is known (FIG. 1) and structural studies on CD4 have shown that this molecule is composed of four extracellular immunoglobulin-like domains (three containing disulfide linked loops). It is also known that the binding of gp120 to its receptor (CD4) induces conformational changes in the Env protein. However only domain 1 (D1) of CD4 is critical for its interaction with gp120 (Arthos et al. (1989) *Cell* 57(3):469-481; Truneh et al. (1991) *J Biol Chem* 266(9):5942-5948). Mutational analyses, antibody competition experiments combined with the knowledge of three-dimensional structure of CD4 have shown that a region homologous to complementarity determining region 2 (CDR2) of immunoglobulin in D1 plays a major role in gp120 binding (Ryu et al. (1994) *Structure* 2(1):59-74, Sullivan et al. (1998) *J Virol* 72(8):6332-6338). Indeed, structure resolution of gp120:CD4 complex confirmed that the CDR2-like loop of CD4 is central in CD4-gp120 interaction (Choe & Sodroski (1992) *J Acquir Immune Defic Syndr* 5(2):204-210, Gizachew et al. (1998) *Biochemistry* 37(30):10616-10625).

Crystallographic structure analysis of gp120, in complex with CD4 and the Fab portion the neutralizing monoclonal antibody 17b (Kwong et al. (1998) *Nature* 393:648-659), indicates that a large surface (742 Å2) of the domain D1 of CD4 binds to a large depression (800 Å2) on gp120. The CD4 interface is comprised by 22 residues, contributing to gp120 binding with mixed hydrophobic, electrostatic, H-bonding interactions. The large size and complexity of this interface makes the reproduction of such functional epitope into a small molecule a challenge, and explains the difficulty in the development of small molecule inhibitors of gp120-CD4 interaction. Vita et al. (1998) *Biopolymers* 47:93-100. However, in spite of the large number of residues present in gp120-CD4 interaction surface, studies on hormone-receptor systems showed that only a few residues might dominate the binding energy at the protein-protein interface. Clackson and Wells (1995) *Science* 267(5196):383-386.

Upon binding of gp120 to CD4, unique neutralizing epitopes also appear to be exposed, for example the epitope recognized by the monoclonal antibody CG10 (Gershoni et al. (1993) *Faseb J* 7(12):1185-1187). Indeed, while monomeric gp120 protein from lab strains is poorly immunogenic with regard to eliciting primary isolate neutralizing antibodies (Mascola et al. (1996) *J. Infect. Dis.* 173:340-348), monoclonal antibodies that appear to recognize certain epitopes that are exposed on the Env surface once it binds to its CD4 receptor have been shown to neutralize diverse primary isolates. See, e.g., the antibody designated 17b (Thali et al. (1993) *J. Virol.* 67(7):3978-88). However, cross-clade primary isolate neutralizing antibody responses using receptor/co-receptor complexed Env have been attributed to the immunogenicity of the gp41 fusion domain. Lacasse et al (1999) *Science* 283:357-362.

Additionally, attempts to evaluate gp120-CD4 complexes as potential vaccine candidate for inducing high avidity and primary isolate neutralizing antibodies have been thwarted by the concern that an immune response could be generated against CD4 itself thereby raising autoimmune and safety issues. (D'Souza et al. (1997) *J. Infect. Dis.* 175:1056-62, DeVico et al. (1995) *Virology* 211(2):583-8).

Thus, the present invention preferably makes use of less than full-length CD4 proteins or CD4 mimetics. The CD4 molecules are combined with an HIV Tat protein to form a hybrid Env-binding molecule that does not induce an immune response against CD4. The hybrid molecules preferably bind to, or are complexed to, an Env protein via the CD4 minimal module. In certain embodiments, the CD4 minimal module portion of the fusion protein comprises amino acid residues 15-85 of SEQ ID NO:1 or a molecule that exhibits structural similarity to a CD4 minimal module (e.g., a CD4 mimetic as described for example in Martin et al. (2003) *Nat. Biotechnol.* 21(1):71-76.). Structural similarity can be determined as described herein. As shown in FIG. 4, a CD4 mini protein comprising residues 15-85 of SEQ ID NO:1 is almost completely buried within the gp120 binding pocket. In addition, this CD4 minimal module is stabilized by the presence of a disulfide bridge between Cys16 and Cys84.

One of skill in the art can readily determine amino acid sequences that exhibit structural and/or amino acid similarity to the CD4 minimal modules described herein in view of the specification. Further, any of these homologs (structural or sequence), can be further modified. Such modifications can affect structure and/or function. For example, amino acid substitutions, additions and/or deletions can be made to the mini-proteins such that the gp120 binding structure is preserved or enhanced.

Any of the CD4 molecules useful in the practice of the invention can be chemically synthesized. Preferably, the synthesis is conducted under conditions that allow and promote efficient folding of the mini-protein into a conformation that binds gp120 and exposes epitopes in or near the CD4 binding site. For example, the mini-protein can be synthesized under conditions that produce a circular dichroism spectrum similar to that of CD4, in spite of mutations in the native sequence.

Tat Polypeptides

The Tat polypeptide component(s) of the hybrid molecules described herein can be derived any known HIV isolates, as well as newly identified isolates, and subtypes of these isolates. Descriptions of structural features can be given herein with reference to SF162 or HXB-2. One of ordinary skill in the art in view of the teachings of the present disclosure and the art can determine corresponding regions in other HIV variants (e.g., isolates $HIV_{IIIb}$, $HIV-1_{SF162}$, $HIV-1_{SF170}$, $HIV_{LAV}$, $HIV_{LAI}$, $HIV_{MN}$, HIV-b $1_{CM235}$, $HIV-1_{US4}$, other HIV-1 strains from diverse subtypes (e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the Tat polypeptide(s) can be based on any HIV variant.

Thus, the Tat polypeptide portion(s) of the hybrid molecules can be selected for any number of characteristics including, their ability to act as scaffold, thereby presenting the CD4 molecules to Env in an overall configuration that mimics CD4. In this way, the binding of the CD4 minimal module-containing hybrid molecule to Env is enhanced while reducing unwanted immune responses to non-Env binding regions of CD4. Proteins exhibiting structural similarity to wild-type CD4 may be identified by performing searches of structural databases, using methods known to those of skill in the art and as described herein. See, also, U.S. Provisional Application Ser. No. 60/578,151, filed June, 2004.

In addition to CD4-like structure (or scaffold) that may provided by the Tat component, the Tat polypeptide may also impart other functions to the hybrid molecules described herein. Other functions of the Tat component include, but are not limited to, immunogenicity, adjuvanticity and/or immunomodulatory characteristics. HIV-1 Tat has been shown in induce strong humoral and cellular responses and animals immunized with Tat vaccines have also been shown to be protected against challenge infection with pathogenic SHIV. See, e.g., Agwale et al. (2002) *Proc. Natl. Acad. Sci. USA*. 99(15):10037-10041; Opi et al. (2002) *J. Biol. Chem.* 277 (39):35915-35919. Thus, in certain embodiments, it may be preferable that the Tat component induces an immune response in the subject (e.g., a Tat-specific immune response), for example a full-length or near full-length Tat polypeptide. Alternatively, in certain embodiments, it may be preferable that one or more immunogenic regions or epitopes of the Tat polypeptides are modified to reduce or eliminate their immunogenicity and/or toxicity.

Accordingly, fusion molecules were designed comprising the CD4 minimal module inserted into sequences encoding various regions of Tat polypeptides (e.g., a Tat polypeptide "scaffold" for the Env-binding portion of CD4). FIG. 5 shows exemplary fusion molecules disclosed herein. See also, Example 1, and FIGS. 6 and 7. The first hybrid molecule depicted in FIG. 5 comprises, in the N-terminal to C-terminal direction, residues 1-20 of a Tat protein, residues 15-85 of CD4 (SEQ ID NO: 1) (CD4 minimal module; and residues 30-86 of a Tat protein. The second hybrid molecule depicted in FIG. 5 comprises, in the N-terminal to C-terminal direction, residues 1-30 of a Tat protein, residues 15-85 of CD4 (SEQ ID NO: 1) (CD4 minimal module; and residues 40-86 of a Tat protein. The third hybrid molecule depicted in FIG. 5 comprises, in the N-terminal to C-terminal direction, residues 1-40 of a Tat protein, residues 15-85 of CD4 (SEQ ID NO: 1) (CD4 minimal module; and residues 50-86 of a Tat protein. The fourth hybrid molecule depicted in FIG. 5 comprises, in the N-terminal to C-terminal direction, residues 1-50 of a Tat protein, residues 15-85 of CD4 (SEQ ID NO: 1) (CD4 minimal module); and residues 60-86 of a Tat protein.

The fusion proteins described herein may also further comprise additional polypeptides including, but not limited to, antigenic polypeptides from one or more pathogens (e.g., viruses such as HIV, HBC, HCV, HAV, RSV, influenza etc or bacteria), immunomodulatory polypeptides such as cytokines, chemokines and the like. For example, the fusion protein may include the Env polypeptide to which the Tat-CD4 hybrid molecule is capable of binding. In this way, a single fusion protein can function as a complex to expose epitopes revealed by CD4 binding. Additional HIV polypeptides may also be included in the fusion protein, for example one or more of Gag, Pol, Prot, Nef, Rev, Tat, Vpu, Vpr, Vif or immunogenic fragments thereof from the same or different strains of HIV.

The tat polypeptides can be provided as polypeptide or polynucleotide encoding the tat polypeptide. In some embodiments, the Tat polynucleotide sequences used are codon optimized.

Env Polypeptides

The Env polypeptide portion of the complexes described herein can be derived from an envelope protein, preferably from HIV Env. As noted above, the envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides.

In certain embodiments, the Env polypeptide component of the complex is a monomer or a dimer. In preferred embodiments, the Env polypeptide component is an oligomeric Env polypeptide. The primary sequence of the Env polypeptide precursor of HIV-1$_{SF2}$ (hereinafter "SF2") strain is known. See, e.g., FIG. 1 of International Publication WO 04/037847, incorporated by reference in its entirety herein. The gp120 amino acid sequence (including leader sequence) extends from approximately amino acids 1-509. The polypeptide contains approximately 24 N-linked glycosylation sites that are common to most, if not all, gp120 sequences. As suggested by their name, the hypervariable domains contain extensive amino acid substitutions, insertions and deletions as between strains. Despite this variation, most, if not all, Env polypeptide sequences preserve the virus's ability to bind to the viral receptor CD4. Further, alignment of the amino acid sequences of Env polypeptide of any HIV variant can be determined relative to other variants, such as HXB-2, as described for example, in WO 00/39303. In other embodiments, the Env polypeptide comprises an oligomeric form of Env, for example oligomeric gp140 (o-gp140).

The Env polypeptide bound or complexed to the CD4-Tat hybrid molecules described herein can be derived any known HIV isolates, as well as newly identified isolates, and subtypes of these isolates. Descriptions of structural features can be given herein with reference to SF2 or HXB-2. One of ordinary skill in the art in view of the teachings of the present disclosure and the art can determine corresponding regions in other HIV variants (e.g., isolates HIV$_{IIIb}$, HIV-1$_{SF162}$, HIV-1$_{SF170}$, HIV$_{LAV}$, HIV$_{LAI}$, HIV$_{MN}$, HIV-1$_{CM235}$, HIV-1$_{US4}$, other HIV-1 strains from diverse subtypes(e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., *Virology*, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that, can identify β-sheet regions). The actual amino acid sequences of the Env polypeptides can be based on any HIV variant.

The Env polypeptides bound by and/or used in complexes with the fusion proteins described herein may include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained. The Env polypeptides described herein can be monomeric or oligomeric.

Polypeptide Production

The CD4 molecules (e.g., CD4 minimal module), Tat polypeptides, Env polypeptides and fusion proteins of the present invention can be produced in any number of ways all of which are well known in the art.

In one embodiment, the polypeptides are generated using recombinant techniques, well known in the art. In this regard, oligonucleotide probes can be devised based on the known sequences of the polypeptide of interest and used to probe genomic or cDNA libraries for the gene(s) encoding the polypeptide. The gene can then be further isolated using standard techniques and, e.g., restriction enzymes employed to truncate the gene at desired portions of the full-length sequence. Similarly, the gene(s) can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the components of the fusion proteins and/or Env polypeptides can be produced synthetically, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone a gene encoding a selected polypeptide gene that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al., (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci. USA* (1982) 79:6409.

Once coding sequences for the desired polypeptides have been isolated or synthesized, they can be cloned into any suitable vector or replicon for expression. As will be apparent from the teachings herein, a wide variety of vectors encoding polypeptides and/or fusion proteins can be generated by creating expression constructs which operably link, in various combinations, polynucleotides encoding CD4 mini proteins and heterologous sequences. Non-limiting examples of such combinations are discussed in the Examples.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-E. call gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the proteins described herein. Generally, such systems use virus-based vectors to transfect plant cells with heterologous genes. For a description of such systems see, e.g., Porta et al., *Mol. Biotech*. (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol*. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter cilia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, for example for the production of an Env polypeptide, the transformed cells secrete the polypeptide product into the surrounding media. Certain regulatory sequences can be included in the vector to enhance secretion of the protein product, for example using a tissue plasminogen activator (TPA) leader sequence, an interferon (alpha or gamma) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the polypeptides (e.g., Env) substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular Env polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described above.

Relatively small polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, The *Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Env-Hybrid Molecule Complexes

Env and the Tat-CD4 molecules described herein can be complexed in a variety of ways. In certain embodiments, Env and the Tat-CD4 molecules are complexed using one or more cross-linking agents or fixatives, such as formaldehyde, formalin, glutyraldehyde and the like The Tat-CD4 needs to be cross-linked with env to maintain the exposure of CD4-inducible epitopes in the Env protein for immunization purposes to target these functional epitopes for vaccine application. Several approaches are available:

1) Classical cross-linking: The traditional approach for covalently cross-linking of proteins is to use non-specific cross-linking agents, such as formaldehyde or glutaraldehyde, which preferentially react with lysine side chains. These reagents are effective at cross-linking CD4-env complexes, because several lysine residues are present at the CD4 and env interface. However, in a preliminary study, we have shown that these reactive agents also modify the antigenic surface of env as reflected by partial preservation of 17b and 4.8d activity. Therefore for determining optimal conditions we need to test different conditions such as pH, buffers and cross-linker concentrations.

2) Advanced cross-linking strategies: Other cross-linking reagents are evaluated based on newer chemistries, such as homo- and hetero-bifunctional reagents of different linker lengths and reactivities. However, it would be ideal to link the Tat-CD4 to Env by a specific covalent bond to a single amino acid residue, thereby preserving the exposed antigenic surface of Env.

3) Cross-linking by mutation of specific amino acid residues in Env: A specific linkage involving the thiol group of a cysteine residue, strategically incorporated into env, may represent a viable method to specifically cross-link Tat-CD4 to Env. However, this strategy will imply a disulfide bridge between Tat-CD4 and env, which will necessarily involve the CD4 binding site. In addition, a disulfide bond is not the most stable covalent bond.

An alternative strategy will be to link CD4 miniprotein-containing fusion protein to the envelope by a specific covalent bond which will not perturb the envelope exposed antigenic surface, yet it will expose the cryptic conserved epitopes that are normally not accessible, for example so that an antibody response can be mounted.

In addition, suitable complexes may be produced by e.g., co-transfecting host cells with constructs encoding the fusion proteins described herein and/or one or more Env polypeptides. In certain embodiments, the Env polypeptides are part of the fusion protein. Thus, co-transfection can be accomplished either in trans or cis, i.e., by using separate vectors or by using a single vector that bears both of the Env and the CD4- and Tat-containing composition. If done using a single vector, both genes can be driven by a single set of control elements. Alternatively, the Env- and CD4/Tat-encoding sequences can be present on the vector in individual expression cassettes, driven by individual control elements. Following expression, the proteins may spontaneously associate. Alternatively, the complexes can be formed by mixing the individual proteins together which have been produced separately, either in purified or semi-purified form, or even by mixing culture media in which host cells expressing the proteins, have been cultured. See, International Publication No. WO 96/04301, published Feb. 15, 1996, for a description of such complexes.

Antibodies

Antibodies, both monoclonal and polyclonal, which are directed against Env-hybrid CD4-Tat molecule complexes epitopes (and cryptic epitopes exposed by binding of CD4 to Env) are particularly useful in diagnosis and therapeutic applications, for example, those antibodies which are neutralizing are useful in passive immunotherapy. Monoclonal antibodies, in particular, may be used to raise anti-idiotype antibodies.

Anti-idiotype antibodies are immunoglobulins that carry an "internal image" of the antigen of the infectious agent against which protection is desired. Techniques for raising anti-idiotype antibodies are known in the art. See, e.g., Grzych (1985) *Nature* 316:74; MacNamara et al (1984) *Science* 226:1325; Uytdehaag et al. (1985) *J. Immunol.* 134: 1225. These anti-idiotype antibodies may also be useful for treatment and/or diagnosis of HIV.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polyclonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated colorimetrically, and related to antigen concentration.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against epitopes exposed by binding of CD4 to Env can also be produced. Normal B cells from a mammal, such as a mouse, immunized with, e.g., an Env-CD4 complex as described herein can be fused with, for example, HAT-sensitive mouse myeloma cells to produce hybridomas. Hybridomas producing antibodies specific for epitopes exposed when CD4 miniproteins bind to Env can be identified using RIA or ELISA and isolated by cloning in semi-solid agar or by limiting dilution. Clones producing the desired specific antibodies are isolated by another round of screening.

Antibodies, either monoclonal and polyclonal, which are directed against epitopes, are particularly useful for detecting the presence of antigens in a sample, such as a serum sample from an HIV-infected human. An immunoassay for an HIV antigen may utilize one antibody or several antibodies. An immunoassay for an HIV antigen may use, for example, a monoclonal antibody directed towards an HIV epitope, a combination of monoclonal antibodies directed towards epitopes of one Env or Env-CD4 minimal module-containing fusion polypeptide, monoclonal antibodies directed towards epitopes of different polypeptides, polyclonal antibodies directed towards the same HIV antigen, polyclonal antibodies directed towards different HIV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Env or fusion protein complexed-Env by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind the target from a biological sample, such as blood or plasma. The bound proteins or complexes are recovered from the column matrix by, for example, a change in pH.

Diagnostic, Vaccine and Therapeutic Applications

The CD4-Tat molecules and complexes comprising these hybrid molecules (e.g., complexes with Env) of the present invention or the polynucleotides coding therefor, can be used for a number of diagnostic and therapeutic purposes. For example, the proteins and polynucleotides or antibodies generated against the same, can be used in a variety of assays, to determine the presence of reactive antibodies/and or Env proteins in a biological sample to aid in the diagnosis of HIV infection or disease status or as measure of response to immunization.

As noted above, the presence of antibodies reactive with the Env (e.g., gp120) polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microliter plates; polyvinylidine fluoride; diazotized paper; nylon membranes; activated beads, and the like.

Typically, the solid support is first reacted with the biological sample (or the gp120 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal.

Alternatively, a "two antibody sandwich" assay can be used to detect the proteins of the present invention. In this technique, the solid support is reacted first with one or more of the antibodies directed against Env (e.g., gp120), washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The complexes described herein, produced as described above, or antibodies to the complexes, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The complexes and polynucleotides encoding the polypeptides can also be used in vaccine compositions, individually or in combination, in e.g., prophylactic (i.e., to prevent infection) or therapeutic (to treat HIV following infection) vaccines. The vaccines can comprise mixtures of one or more of the modified Env proteins (or nucleotide sequences encoding the proteins), such as Env (e.g., gp120) proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125-ser125), GM-CSF, IL-12, -interferon, IP-10, MIP1 and RANTES. The vaccines may be administered as polypeptides or, alternatively, as naked nucleic acid vaccines (e.g., DNA), using viral vectors (e.g., retroviral vectors, adenoviral vectors, adeno-associated viral vectors) or non-viral vectors (e.g., liposomes, particles coated with nucleic acid or protein). The vaccines may also comprise a mixture of protein and nucleic acid, which in turn may be delivered using the same or different vehicles. The vaccine may be given more than once (e.g., a "prime" administration followed by one or more "boosts") to achieve the desired effects. The same composition can be administered as the prime and as the one or more boosts. Alternatively, different compositions can be used for priming and boosting.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the Env polypeptide may be conjugated to a bacterial toxoid, such as toxoid from diphtheria, tetanus, cholera, etc.

Adjuvants may also be used to enhance the effectiveness of the vaccines.

Adjuvants

Vaccines of the invention may be administered in conjunction with other immunoregulatory agents. In particular, compositions will usually include an adjuvant.

Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

B. Oil-Emulsions

Oil-emulsion compositions suitable for use as adjuvants in the invention include squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", *Vaccine* (2001) 19: 2673-2680; Frey et al., "Comparison of the safety, tolerability, and immunogenicity of a MF59-adjuvanted influenza vaccine and a non-adjuvanted influenza vaccine in non-elderly adults", *Vaccine* (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott at al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the invention.

C. Saponin Formulations

Saponin formulations may also be used as adjuvants in the invention. Saponins are a heterologous group of sterol glycosides and triterpenoid glycosides that are found in the bark, leaves, stems, roots and even flowers of a wide range of plant species.

Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs, Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr et al., "ISCOMs and other saponin based adjuvants", *Advanced Drug Delivery Reviews* (1998) 32:247-271. See also Sjolander, et al., "Uptake and adjuvant activity of orally delivered saponin and ISCOM vaccines", *Advanced Drug Delivery Reviews* (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", *Virology* (2002) 293:273-280; Lenz et al., "Papillomarivurs-Like Particles Induce Acute Activation of Dendritic Cells", *J. Immunology* (2001) 5246-5355; Pinto et al., "Cellular Immune Responses to Human Papillomavirus (HPV)-16 L1 Healthy Volunteers Immunized with Recombinant HPV-16 L1 Virus-Like Particles", *J. Infectious Diseases* (2003) 188: 327-338; and Gerber et al., "Human Papillomavirus Virus-Like Particles Are Efficient Oral Immunogens when Coadministered with *Escherichia coli* Heat-Labile Entertoxin Mutant R192G or CpG", *J. Virology* (2001) 75(10):4752-4760. Virosomes are discussed further in, for example, Gluck et al., "New Technology Platforms in the Development of Vaccines for the Future", *Vaccine* (2002) 20:B10-B16. Immunopotentiating reconstituted influenza virosomes (IRIV) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", *Vaccine* (2003) 21:2485-2491; and Pajak et al., "The Adjuvant OM-174 induces both the migration and maturation of murine dendritic cells in vivo", *Vaccine* (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded, Optionally, the guanosine may be replaced with an analog such as 2'-deoxy-7-deazaguanosine. See Kandimalla et al., "Divergent synthetic nucleotide motif recognition pattern: design and development of potent immunomodulatory oligodeoxyribonucleotide agents with distinct cytokine induction profiles", *Nucleic Acids Research* (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", *Nature Medicine* (2003) 9(7): 831-835; McCluskie et al., "Parenteral and mucosal prime-boost immunization strategies in mice with hepatitis B surface antigen and CpG DNA", *FEMS Immunology and Medical Microbiology* (2002) 32:179-185; WO98/40100; U.S. Pat. Nos. 6,207,646, 6,239,116 and 6,429,199.

The CpG sequence may be directed to TLR9, such as the motif GTCGTT or TTCGTT. See Kandimalla et al., "Toll-like receptor 9: modulation of recognition and cytokine induction by novel synthetic CpG DNAs", *Biochemical Soci-* ety Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al., "CpG-A-Induced Monocyte IFN-gamma-Inducible Protein-10 Production is Regulated by Plasmacytoid Dendritic Cell Derived IFN-alpha", *J. Immunol.* (2003) 170(8):4061-4068; Krieg, "From A to Z on CpG", *TRENDS in Immunology* (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al., "Secondary structures in CpG oligonucleotides affect immunostimulatory activity", *BBRC* (2003) 306:948-953; Kandimalla et al., "Toll-like receptor 9: modulation of recognition and cytokine induction by novel synthetic GpG DNAs", *Biochemical Society Transactions* (2003) 31(part 3):664-658; Bhagat et al., "CpG penta- and hexadeoxyribonucleotides as potent immunomodulatory agents" *BBRC* (2003) 300:853-861; and WO03/035836.

(4) ADP-Ribosylating Toxins and Detoxified Derivatives Thereof.

Bacterial ADP-ribosylating toxins and detoxified derivatives thereof may be used as adjuvants in the invention. Preferably, the protein is derived from *E. coli* (i.e., *E. coli* heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al., "The LTR72Mutant of Heat-Labile Enterotoxin of *Escherichia coli* Enhances the Ability of Peptide Antigens to Elicit CD4+T Cells and Secrete Gamma Interferon after Coapplication onto Bare Skin", *Infection and Immunity* (2002) 70(6): 3012-3019; Pizza et al., "Mucosal vaccines: non toxic derivatives of LT and CT as mucosal adjuvants", *Vaccine* (2001) 19:2534-2541; Pizza et al., "LTK63 and LTR72, two mucosal adjuvants ready for clinical trials" *Int. J. Med. Microbiol.* (2000) 290(4-5):455-461; Scharton-Kersten et al., "Transcutaneous Immunization with Bacterial ADP-Ribosylating Exotoxins, Subunits and Unrelated Adjuvants", *Infection and Immunity* (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" *Infection and Immunity* (1999) 67(12):6270-6280; Partidos et al., "Heat-labile enterotoxin of *Escherichia coli* and its site-directed mutant LTK63 enhance the proliferative and cytotoxic T-cell responses to intranasally co-immunized synthetic peptides", *Immunol. Lett.* (1999) 67(3):209-216; Peppoloni et al., "Mutants of the *Escherichia coli* heat-labile enterotoxin as safe and strong adjuvants for intranasal delivery of vaccines", *Vaccines* (2003) 2(2):285-293; and Pine et al., (2002) "Intranasal immunization with influenza vaccine and a detoxified mutant of heat labile enterotoxin from *Escherichia coli* (LTK63)"*J. Control Release* (2002) 85(1-3):263-270. Numerical reference for amino acid substitutions is preferably based on the alignments of the A and B subunits of ADP-ribosylating toxins set forth in Domenighini et al., *Mol. Microbiol.* (1995) 15(6):1165-1167.

F. Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethyl-cellulose. Chitosan and derivatives thereof may also be used as adjuvants in the invention (see, e.g. WO99/27960).

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. Nos. 6,090,406, 5,916, 588, and EP 0 626 169.

I. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", *Biomaterials* (1998) 19(1-3):109-115 and Payne et al., "Protein Release from Polyphosphazene Matrices", *Adv. Drug. Delivery Review* (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds.

Examples of imidazoquinoline compounds suitable for use adjuvants in the invention include Imiquimod and its analogues, described further in Stanley, "Imiquimod and the imidazoquinolines: mechanism of action and therapeutic potential" *Clin Exp Dermatol* (2002) 27(7):571-577; Jones, "Resiquimod 3M", *Curr Opin Investig Drugs* (2003) 4(2): 214-218; and U.S. Pat. Nos. 4,689,338, 5,389,640, 5,268, 376, 4,929,624, 5,266,575, 5,352,784, 5,494,916, 5,482,936, 5,346,905, 5,395,937, 5,238,944, and 5,525,612.

M. Thiosemicarbazone Compounds.

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

N. Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention:

(1) a saponin and an oil-in-water emulsion (WO99/11241);
(2) a saponin (e.g., QS21)+a non-toxic LPS derivative (e.g. 3dMPL) (see WO94/00153);
(3) a saponin (e.g., QS21)+a non-toxic LPS derivative (e.g. 3dMPL)+a cholesterol;
(4) a saponin (e.g. QS21)+3dMPL+IL-12 (optionally+a sterol) (WO98/57659);
(5) combinations of 3dMPL with, for example, QS21 and/or oil-in-water emulsions (See European patent applications 0835318, 0735898 and 0761231);
(6) SAF, containing 10% Squalane, 0.4% Tween 80, 5% pluronic-block polymer L121, and thr-MDP, either microfluidized into a submicron emulsion or vortexed to generate a larger particle size emulsion.
(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and
(8) one or more mineral salts (such as an aluminum salt)+a non-toxic derivative of LPS (such as 3dPML).
(9) one or more mineral salts (such as an aluminum salt)+ an immunostimulatory oligonucleotide (such as a nucleotide sequence including a CpG motif).

O. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the hybrid molecules or complexes described herein, or further complexes of these complexes, or nucleotide sequences encoding the same, antibodies directed to these complexes and any other of the above-mentioned components, as needed. By "therapeutically effective amount" is meant an amount that will induce a protective immunological response in the uninfected, infected or unexposed individual to whom it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell. Antibodies may, e.g., be neutralizing in nature, may generate an Antibody Dependent Cell, mediated Cytotoxicity, or may synergistically interact with other antibodies having such activity or with Cell mediated responses to viral infection and or replication.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the complex selected and its mode of administration, among other factors. An appropriate effective amount can be readily determined by one of skill in the art. A "therapeutically effective amount" will fall in a relatively broad range that can be determined through routine trials.

Once formulated, the nucleic acid vaccines may be accomplished with or without viral vectors, as described above, by injection using either a conventional syringe or a gene gun, such as the Accell® gene delivery system (PowderJect Technologies, Inc., Oxford, England). Delivery of DNA into cells of the epidermis is particularly preferred as this mode of administration provides access to skin-associated lymphoid cells and provides for a transient presence of DNA in the recipient. Both nucleic acids and/or peptides can be injected or otherwise administered either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Design of Hybrid Proteins Comprising Tat Polypeptides and a CD4 Minimal Module Novel hybrid proteins comprising the env binding region of human CD4 were designed as follows. The three-dimensional (3D) structure of CD4-gp120 was analyzed and a region of CD4 involved in env binding was identified. In particular, the region corresponding to amino acid residues 15-85 of CD4 is almost completely buried within the CD4-binding pocket of env (FIG. 4). This fragment was termed a CD4 minimal module and the fragment is stabilized by the presence of a disulfide bridge between Cys16 and Cys84.

Subsequently, standard molecular biological techniques were used to clone the CD4 minimal module (residues 15-85) into various expression cassettes in order to express a Tat-CD4 fusion protein. The expression cassettes included sequences encoding the CD4 minimal module flanked by sequences encoding Tat polypeptides. In particular, as shown in FIG. 5, the expression cassettes include sequences encoding, in a 5'-3' direction, residues 1-20 of Tat, residues 15-85 of CD4 (CD4 minimal module), residues 30-86 of Tat; or sequences encoding, in a 5'-3' direction, residues 1-30 of Tat, residues 15-85 of CD4 (CD4 minimal module), residues 40-86 of Tat; or sequences encoding, in a 5'-3' direction, residues 1-40 of Tat, residues 15-85 of CD4 (CD4 minimal module), residues 50-86 of Tat; or sequences encoding, in a 5'-3' direction, residues 1-50 of Tat, residues 15-85 of CD4 (CD4 minimal module), residues 60-86 of Tat.

293 cells were transfected with the different Tat-CD4 fusion constructs (having a part of CD4 in fusion with the Tat gene), described above. Cells were grown in regular 293 media as described in Srivastava et al. (2003) (*J. Virol.* 77(20): 11244-11259). Seventy-two hours after transfection, supernatants were collected and lysates were prepared by using a buffer containing NP40 (0.5%) (Sigma, St. Louis, Mo.). The lysate and supernatant samples (15 μl per lane) were loaded onto a Bis Tris gel (Invitrogen, Carlsbad, Calif.), as described in Srivastava et al. (2003) (*J. Virol.* 77(20):11244-11259). Material from the gel was transferred on to a nitrocellulose membrane, and blot was probed with anti-CD4 monoclonal antibody, as well as anti-Tat mouse polyclonal sera (1:400 dilution) and anti-B actin (1:500 dilution) as described in Srivastava et al. (2003) (*J. Virol.* 77(20):11244-11259) (anti-mouse florescence conjugated antibody, was used at 1:30000 dilution, and detected by Odyssey method).

Figure 9:
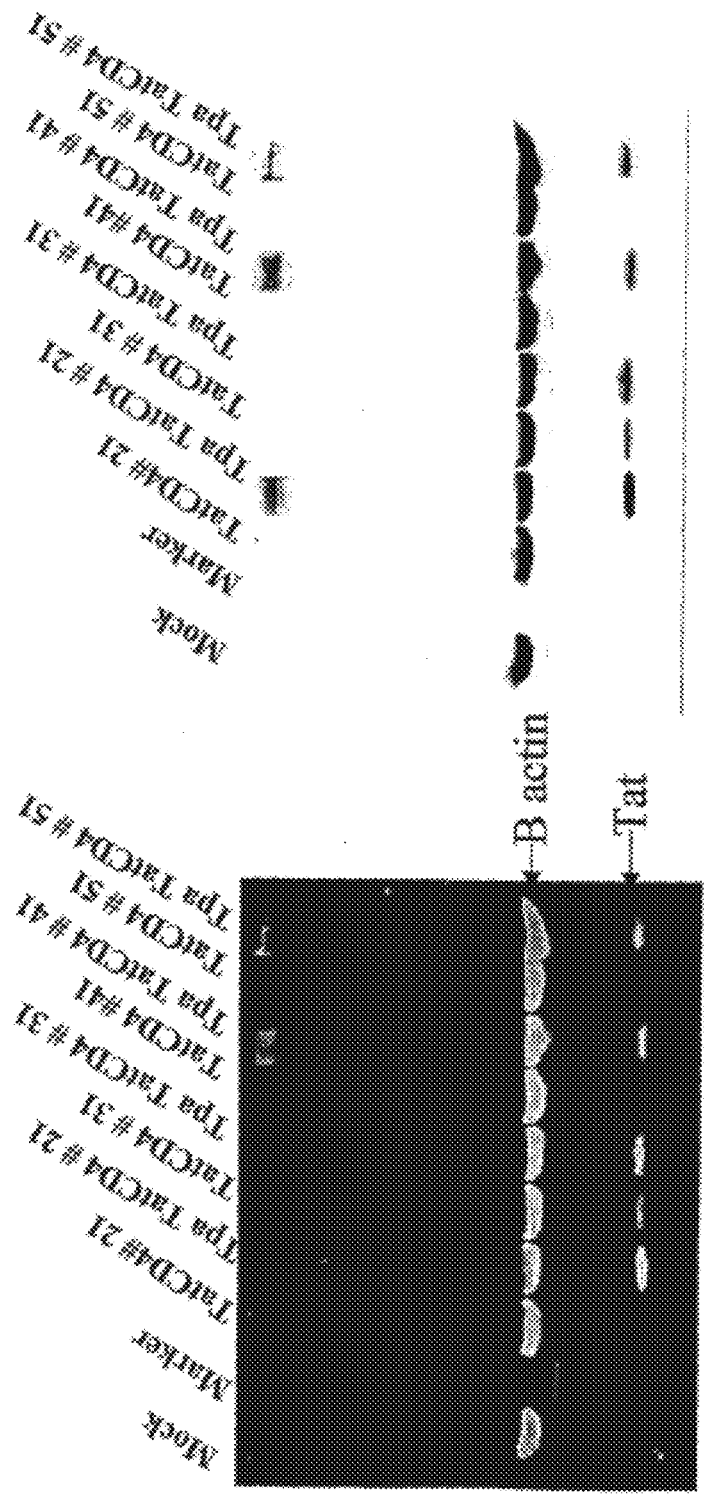
FIG. 9 depicts results showing expression of various Tat-CD4 fusion constructions.

As shown in FIG. 9, Tat is recognized by the anti-Tat antibody suggesting that by introducing CD4 minimal domain in the Tat gene at different positions did not compromise Tat expression. It is evident that there are some differences in the expression profile between the constructs with and without tissue plasminogen activator leader (tPA) sequence. With the exception of construct #31, there was negligible expression of Tat-CD4 without tPA. However, it seems that the expression was improved by adding a tPA leader sequence. Studies may be conducted to demonstrate the Tat-CD4 fusion protein has retained the ability to bind to HIV Env, and induce the conformational change.

When expressed, the fusion protein includes the Env binding site of CD4 while reducing unwanted CD4 epitopes and also includes Tat polypeptides that can elicit a Tat-specific immune response. Various embodiments of env protein monomers and oligomers can be bound to the Tat-CD4 hybrid fusion molecule, including gp120, gp140 and gp160, and variants thereof.

Example 2

Preparation of Env-Fusion Protein Complexes

Stable purified env-hybrid protein complexes are prepared with and without formaldehyde treatment. For example, to induce conformational changes in env, equimolar concentration of env (e.g. SF2 or SF162) and hybrid molecules comprising a CD4 minimal module and one or more Tat polypeptides are incubated together at 37° C. for one hour. At the cellular level, these interactions are transient. Therefore, at the end of incubation, half of the complexes are fixed with formaldehyde while the other half remain untreated. Both the treated and untreated complexes are separated on Superdex-200 column. Purified fractions are analyzed on an HPLC column and on SDS-PAGE. The purified complexes contain both env and fusion proteins together. Furthermore, these complexes are expected to be homogeneous and will not contain more than 2-3% of free fusion protein.

The ability of Env to complex to the hybrid molecules is monitored by the induction of CD4 inducible epitopes recognized by MAbs 17b and 4.8d using standard techniques. In particular, purified chimerae produced in the SF162 Env background, then, are characterized by surface plasmon resonance (SPR) to evaluate exposure of CD4i epitopes and by co-receptor binding tests to evaluate their binding affinities. See, also Devico et al. (1996) *Virology* 218:258-263 and Zhang et al. (1999) *Biochemistry* 38(29):9405-9416 which show SPR testing of another CD4 miniprotein and that the CD4 miniproteins are able to compete with sCD4 for binding to the same env site, and to induce envelope conformational changes, as detected by the monoclonal antibody 17b (Sullivan et al. (1998) *J. Virol.* 72(8):6332-6338). This antibody recognizes an epitope located near the gp120 V3 loop and consisting mainly of the conserved stem of V1/V2, which is probably masked by the flanking V1N2 and V3 loops (Kwong et al. (1998) *Nature* (London) 393:648-659; Rizzuto et al. (1998) Science 280:1949-1953) but exposed in the env complexed to CD4. The effect of miniprotein addition on antibody maximum binding and association rate increase was small, probably reflecting its low env binding affinity, but specific and easily detected. These procedures are applicable to gp120, gp140 and gp160 monomers, oligomers and variants thereof (e.g., to preparation of stable purified hybrid protein complexes). Such variants include, for example, deletions of beta sheets and V2/V3 loop deletions in env, and the like.

Example 3

Neutralizing Antibody Production

Vaccines comprising compositions of the invention can be delivered by various routes known in the art, including, e.g., delivery of a polypeptide antigen and/or delivery of a polynucleotide expressing the polypeptide in one or more dosings. For example, the DNA prime/protein boost strategy allows for screening of multiple Env structures in rabbits and non-human primates with the potential for epitope presentation in situ in the host when delivered as DNA vaccines. DNA vaccination can comprise administration of naked DNA, DNA e.g., complexed to microparticles (such as FLG particles), or DNA as part of a viral vector, and can be followed with protein boosting. Electroporation or DNA vaccination by use of a viral vector and other methods described herein are used to efficiently deliver polynucleotides encoding the hybrid proteins and/or Env polypeptides to non-human mammals (e.g., primates).

A. CD4-Tat Hybrid Protein-Env Complexes

Groups of 4-5 or more rabbits each are immunized at 0, 4, 12 and 24 weeks. Sera are collected biweekly and analyzed against, e.g., SF2 gp120 or SF162 gp120 in an ELISA. These animals mount a strong immune response against gp120. In addition to anti-gp120 responses, these complexes also induced strong anti-CD4 response, as expected.

Thus, the rationally designed fusion protein including a CD4 miniprotein, bound with high affinity to different envelope forms (including oligomeric and monomeric forms of SF162 with and without V2-deletes), induce conformational changes in these proteins and induce full exposition of conserved cryptic CD4 inducible epitopes and/or co-receptor binding sites. Thus, the fusion proteins may be useful in complex with envelope protein to expose envelope epitopes to neutralizing antibodies thus may find potential application in vaccine formulations.

B. Env-CD4/Tat Protein Constructs

Groups of 4-5 or more rabbits each are immunized at 0, 4, 12 and 24 weeks. Sera are collected biweekly and analyzed in an ELISA. Complexes identified by these rabbit studies are then tested in macaques.

C. Monkeys

Groups of 5 or more monkeys are immunized with Env-CD4/Tat complexes or Env-CD4/Tat proteins constructs with adjuvant along with control groups of Env protein only and CD4/Tat molecules only. Complexes are made with monomeric and oligomeric forms of SF162 Env with and without V2-deletes and the antibody responses in rabbits compared. Immunization schedules are at 0, 4 and 24 weeks immunizations; when warranted, an additional booster may be included at later time points.

Example 4

Unmasking Cryptic Epitopes of GP41 Subunit in Oligomeric Envelopes

CD4 minimal modules and fusions comprising these minimal modules can induce a conformational transformation of oligomeric (o-gp140) envelopes, unmasking cryptic epitopes, close to co-receptor sites in gp120 subunit and efficiently increases co-receptor binding affinity in different gp120 envelopes. The induction of this conformational transformation by CD4 minimal modules and fusions comprising these CD4 miniproteins, binding in the different oligomeric Env structures is tested, using SPR technology and 2F5 mAb or DP178 peptides (or congeners). The effect of addition of peptides from the N-terminal domain of CCR5 co-receptor, which have been shown to bind to gp120 is also examined.

If exposition of gp41 epitopes is demonstrated, the peptides are chemically coupled to the CD4 fusion proteins, to produce novel bi-functional ligands, presenting increased potency in unmasking gp41 epitopes. Novel chimeric oligomeric envelopes, incorporating the bi-functional ligands are also produced chemically or genetically, and tested. Candidate envelope proteins with superior exposure of gp120 and gp41 cryptic epitopes are then tested in animals for the induction of neutralizing antibodies.

Example 5

Production of Monoclonal Antibodies Targeting Cryptic Conserved Epitopes of ENV

Selected fusion proteins and complexes comprising these fusion proteins immunogens will be injected in rats to prepare monoclonal antibodies, according to the standard procedures. Clones will be screened in ELISA against CD4 miniprotein-gp120 complex, CD4 miniprotein fusion proteins complexed to o-gp140, o-gp140, gp120 and o-gp140 alone. All the clones exhibiting highest affinity for complexes as compared to envelopes alone will be further tested in Biacore. All the clones scoring positive in Biacore against the CD4M33-gp120 and or CD4M33-o-gp140 complexes will be selected and used for bulk production of ascites fluids.

The invention claimed is:

1. A method of generating an immune response in a subject, the method comprising:
   administering an immunogenic composition comprising a hybrid Env-binding molecule to a subject under conditions that allow production of antibodies in the subject, wherein the hybrid Env-binding molecule comprises a CD4 mini-protein comprising amino acid residues 15-85 of SEQ ID NO: 1 and inserted into a human immunodeficiency virus-1 (HIV-1) Tat scaffold polypeptide,
   wherein the hybrid Env-binding molecule is conjugated to an HIV-1 Env polypeptide, and
   wherein the immune response comprises the elicitation of neutralizing antibodies against a cryptic HIV Envelope epitope in or near the CD4-binding site or in or near the chemokine receptor-binding site.

2. The method of claim 1, wherein the HIV-1 Env polypeptide comprises gp 120 or oligomeric gp 140.

3. The method of claim 1, further comprising isolating the antibodies produced in the subject.

4. The method of claim 1, wherein the antibodies are monoclonal antibodies.

5. The method of claim 1, wherein the antibodies are polyclonal antibodies.

6. The method of claim 1, wherein an immune response to CD4 is not elicited.

7. The method of claim 1, wherein the HIV-1 Tat scaffold polypeptide is derived from one or more full length Tat proteins.

8. The method of claim 1, wherein the HIV-1 Tat scaffold polypeptide is derived from a one or more fragments of a Tat protein.

9. The method of claim 8, wherein the one or more fragments of a Tat protein comprises, in the N-terminal to C-terminal direction, amino acid residues 1-20 of an HIV-1 Tat protein.

10. The method of claim 9, wherein the one or more fragments of a Tat protein comprises, in the N-terminal to C-terminal direction, amino acid residues 1-30 of an HIV-1 Tat protein.

11. The method of claim 10, wherein the one or more fragments of a Tat protein comprises, in the N-terminal to C-terminal direction, amino acid residues 1-40 of an HIV-1 Tat protein.

12. The method of claim 11, wherein the one or more fragments of a Tat protein comprises, in the N-terminal to C-terminal direction, amino acid residues 1-50 of an HIV-1 Tat protein.

13. The method of claim 8, wherein the one or more fragments of a Tat protein comprises, in the N-terminal to C-terminal direction, amino acid residues 60-86 of an HIV-1 Tat protein.

14. The method of claim 13, wherein the one or more fragments of a Tat protein comprises, in the N-terminal to C-terminal direction, amino acid residues 50-86 of an HIV-1 Tat protein.

15. The method of claim 14, wherein the one or more fragments of a Tat protein comprises, in the N-terminal to C-terminal direction, amino acid residues 40-86 of an HIV-1 Tat protein.

16. The method of claim 15, wherein the one or more fragments of a Tat protein comprises, in the N-terminal to C-terminal direction, amino acid residues 30-86 of an HIV-1 Tat protein.

17. The method of any one of claims 9-16, wherein the amino acid residues are numbered relative to SEQ ID NO: 2 or SEQ ID NO: 3.

18. The method of claim 1, wherein the immunogenic composition further comprises an adjuvant.

19. The method of claim 1, wherein the hybrid Env-binding molecule and the HIV-1 Env polypeptide are complexed using a cross-linking agent.

20. The method of claim 19, wherein the cross-linking agent is selected from the group consisting of formaldehyde, formalin, and glutyraldehyde.

* * * * *

SEQUENCE LISTING

```
<160> NUMBER OF SEQ ID NOS: 13

<210> SEQ ID NO 1
<211> LENGTH: 433
<212> TYPE: PRT
<213> ORGANISM: Homo sapiens

<400> SEQUENCE: 1

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110
```

```
Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
                180                 185                 190

Gln Val Glu Phe Ser Phe Pro Leu Ala Phe Thr Val Glu Lys Leu Thr
            195                 200                 205

Gly Ser Gly Glu Leu Trp Trp Gln Ala Glu Arg Ala Ser Ser Ser Lys
            210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
                260                 265                 270

Thr Leu Ala Leu Glu Ala Lys Thr Gly Lys Leu His Gln Glu Val Asn
            275                 280                 285

Leu Val Val Met Arg Ala Thr Gln Leu Gln Lys Asn Leu Thr Cys Glu
            290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
                340                 345                 350

Val Leu Leu Glu Ser Asn Ile Lys Val Leu Pro Thr Trp Ser Thr Pro
            355                 360                 365

Val Gln Pro Met Ala Leu Ile Val Leu Gly Gly Val Ala Gly Leu Leu
            370                 375                 380

Leu Phe Ile Gly Leu Gly Ile Phe Phe Cys Val Arg Cys Arg His Arg
385                 390                 395                 400

Arg Arg Gln Ala Glu Arg Met Ser Gln Ile Lys Arg Leu Leu Ser Glu
                405                 410                 415

Lys Lys Thr Cys Gln Cys Pro His Arg Phe Gln Lys Thr Cys Ser Pro
            420                 425                 430

Ile

<210> SEQ ID NO 2
<211> LENGTH: 86
<212> TYPE: PRT
<213> ORGANISM: Human immunodeficiency virus

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45
```

```
Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 3
<211> LENGTH: 101
<212> TYPE: PRT
<213> ORGANISM: Human immunodeficiency virus

<400> SEQUENCE: 3

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Gly Leu Gly Ile Ser Tyr Gly
            35                  40                  45

Arg Lys Lys Arg Arg Gln Arg Arg Ala Pro Pro Asp Ser Glu Val
        50                  55                  60

His Gln Val Ser Leu Pro Lys Gln Pro Ala Ser Gln Pro Gln Gly Asp
65                  70                  75                  80

Pro Thr Gly Pro Lys Glu Ser Lys Lys Val Glu Arg Glu Thr Glu
                85                  90                  95

Thr Asp Pro Val His
                100

<210> SEQ ID NO 4
<211> LENGTH: 147
<212> TYPE: PRT
<213> ORGANISM: Artificial Sequence
<220> FEATURE:
<223> OTHER INFORMATION: Tat-CD4 fusion protein

<400> SEQUENCE: 4

Met Glu Pro Val Asp Pro Arg Leu Glu Pro Trp Lys His Pro Gly Ser
1               5                   10                  15

Gln Pro Lys Thr Thr Cys Thr Ala Ser Gln Lys Lys Ser Ile Gln Phe
                20                  25                  30

His Trp Lys Asn Ser Asn Gln Ile Lys Ile Leu Gly Asn Gln Gly Ser
            35                  40                  45

Phe Leu Thr Lys Gly Pro Ser Lys Leu Asn Asp Arg Ala Asp Ser Arg
50                  55                  60

Arg Ser Leu Trp Gln Gly Asn Phe Pro Leu Ile Ile Lys Asn Leu Lys
65                  70                  75                  80

Ile Glu Asp Ser Asp Thr Tyr Ile Cys Glu Cys Cys Phe His Cys Gln
                85                  90                  95

Val Cys Phe Thr Thr Lys Ala Leu Gly Ile Ser Tyr Gly Arg Lys Lys
                100                 105                 110

Arg Arg Gln Arg Arg Pro Pro Gln Gly Ser Gln Thr His Gln Val
        115                 120                 125

Ser Leu Ser Lys Gln Pro Thr Ser Gln Pro Arg Gly Asp Pro Thr Gly
        130                 135                 140

Pro Lys Glu
145

<210> SEQ ID NO 5
```

```
<211> LENGTH: 146
<212> TYPE: PRT
<213> ORGANISM: Artificial Sequence
<220> FEATURE:
<223> OTHER INFORMATION: Tat-CD4 fusion protein

<400> SEQUENCE: 5

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Thr Cys
            20                  25                  30

Thr Ala Ser Gln Lys Lys Ser Ile Gln Phe His Trp Lys Asn Ser Asn
        35                  40                  45

Gln Ile Lys Ile Leu Gly Asn Gln Gly Ser Phe Leu Thr Lys Gly Pro
    50                  55                  60

Ser Lys Leu Asn Asp Arg Ala Asp Ser Arg Arg Ser Leu Trp Gln Gly
65                  70                  75                  80

Asn Phe Pro Leu Ile Ile Lys Asn Leu Lys Ile Glu Asp Ser Asp Thr
                85                  90                  95

Tyr Ile Cys Glu Lys Ala Leu Gly Ile Ser Tyr Gly Arg Lys Lys Arg
            100                 105                 110

Arg Gln Arg Arg Arg Pro Pro Gln Gly Ser Gln Thr His Gln Val Ser
        115                 120                 125

Leu Ser Lys Gln Pro Thr Ser Gln Pro Arg Gly Asp Pro Thr Gly Pro
    130                 135                 140

Lys Glu
145

<210> SEQ ID NO 6
<211> LENGTH: 147
<212> TYPE: PRT
<213> ORGANISM: Artificial Sequence
<220> FEATURE:
<223> OTHER INFORMATION: Tat-CD4 fusion protein

<400> SEQUENCE: 6

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Thr Cys Thr Ala Ser Gln Lys Lys
        35                  40                  45

Ser Ile Gln Phe His Trp Lys Asn Ser Asn Gln Ile Lys Ile Leu Gly
    50                  55                  60

Asn Gln Gly Ser Phe Leu Thr Lys Gly Pro Ser Lys Leu Asn Asp Arg
65                  70                  75                  80

Ala Asp Ser Arg Arg Ser Leu Trp Gln Gly Asn Phe Pro Leu Ile Ile
                85                  90                  95

Lys Asn Leu Lys Ile Glu Asp Ser Asp Thr Tyr Ile Cys Glu Lys Lys
            100                 105                 110

Arg Arg Gln Arg Arg Arg Pro Pro Gln Gly Ser Gln Thr His Gln Val
        115                 120                 125

Ser Leu Ser Lys Gln Pro Thr Ser Gln Pro Arg Gly Asp Pro Thr Gly
    130                 135                 140

Pro Lys Glu
145

<210> SEQ ID NO 7
```

```
<211> LENGTH: 147
<212> TYPE: PRT
<213> ORGANISM: Artificial Sequence
<220> FEATURE:
<223> OTHER INFORMATION: Tat-CD4 fusion protein

<400> SEQUENCE: 7

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
                20                  25                  30

His Cys Gln Val Cys Phe Thr Thr Lys Ala Leu Gly Ile Ser Tyr Gly
            35                  40                  45

Arg Lys Thr Cys Thr Ala Ser Gln Lys Lys Ser Ile Gln Phe His Trp
        50                  55                  60

Lys Asn Ser Asn Gln Ile Lys Ile Leu Gly Asn Gln Gly Ser Phe Leu
65                  70                  75                  80

Thr Lys Gly Pro Ser Lys Leu Asn Asp Arg Ala Asp Ser Arg Arg Ser
                85                  90                  95

Leu Trp Gln Gly Asn Phe Pro Leu Ile Ile Lys Asn Leu Lys Ile Glu
            100                 105                 110

Asp Ser Asp Thr Tyr Ile Cys Glu Gln Gly Ser Gln Thr His Gln Val
        115                 120                 125

Ser Leu Ser Lys Gln Pro Thr Ser Gln Pro Arg Gly Asp Pro Thr Gly
    130                 135                 140

Pro Lys Glu
145

<210> SEQ ID NO 8
<211> LENGTH: 146
<212> TYPE: PRT
<213> ORGANISM: Artificial Sequence
<220> FEATURE:
<223> OTHER INFORMATION: Tat-CD4 fusion protein

<400> SEQUENCE: 8

Met Glu Pro Val Asp Pro Arg Leu Glu Pro Trp Lys His Pro Gly Ser
1               5                   10                  15

Gln Pro Lys Thr Thr Cys Thr Ala Ser Gln Lys Lys Ser Ile Gln Phe
                20                  25                  30

His Trp Lys Asn Ser Asn Gln Ile Lys Ile Leu Gly Asn Gln Gly Ser
            35                  40                  45

Phe Leu Thr Lys Gly Pro Ser Lys Leu Asn Asp Arg Ala Asp Ser Arg
        50                  55                  60

Arg Ser Leu Trp Gln Gly Asn Phe Pro Leu Ile Ile Lys Asn Leu Lys
65                  70                  75                  80

Ile Glu Asp Ser Asp Thr Tyr Ile Cys Glu Cys Cys Phe His Cys Gln
                85                  90                  95

Val Cys Phe Ile Thr Lys Gly Leu Gly Ile Ser Tyr Gly Arg Lys Lys
            100                 105                 110

Arg Arg Gln Arg Arg Ala Pro Pro Asp Ser Glu Val His Gln Ser
        115                 120                 125

Leu Pro Lys Gln Pro Ala Ser Gln Pro Gln Gly Asp Pro Thr Gly Pro
    130                 135                 140

Lys Glu
145

<210> SEQ ID NO 9
```

```
<211> LENGTH: 146
<212> TYPE: PRT
<213> ORGANISM: Artificial Sequence
<220> FEATURE:
<223> OTHER INFORMATION: Tat-CD4 fusion protein

<400> SEQUENCE: 9

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Thr Cys
            20                  25                  30

Thr Ala Ser Gln Lys Lys Ser Ile Gln Phe His Trp Lys Asn Ser Asn
        35                  40                  45

Gln Ile Lys Ile Leu Gly Asn Gln Gly Ser Phe Leu Thr Lys Gly Pro
    50                  55                  60

Ser Lys Leu Asn Asp Arg Ala Asp Ser Arg Arg Ser Leu Trp Gln Gly
65                  70                  75                  80

Asn Phe Pro Leu Ile Ile Lys Asn Leu Lys Ile Glu Asp Ser Asp Thr
                85                  90                  95

Tyr Ile Cys Glu Thr Lys Gly Leu Gly Ile Ser Tyr Gly Arg Lys Lys
            100                 105                 110

Arg Arg Gln Arg Arg Arg Ala Pro Pro Asp Ser Glu Val His Gln Ser
        115                 120                 125

Leu Pro Lys Gln Pro Ala Ser Gln Pro Gln Gly Asp Pro Thr Gly Pro
    130                 135                 140

Lys Glu
145

<210> SEQ ID NO 10
<211> LENGTH: 146
<212> TYPE: PRT
<213> ORGANISM: Artificial Sequence
<220> FEATURE:
<223> OTHER INFORMATION: Tat-CD4 fusion protein

<400> SEQUENCE: 10

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Thr Cys Thr Ala Ser Gln Lys Lys
        35                  40                  45

Ser Ile Gln Phe His Trp Lys Asn Ser Asn Gln Ile Lys Ile Leu Gly
    50                  55                  60

Asn Gln Gly Ser Phe Leu Thr Lys Gly Pro Ser Lys Leu Asn Asp Arg
65                  70                  75                  80

Ala Asp Ser Arg Arg Ser Leu Trp Gln Gly Asn Phe Pro Leu Ile Ile
                85                  90                  95

Lys Asn Leu Lys Ile Glu Asp Ser Asp Thr Tyr Ile Cys Glu Lys Lys
            100                 105                 110

Arg Arg Gln Arg Arg Arg Ala Pro Pro Asp Ser Glu Val His Gln Ser
        115                 120                 125

Leu Pro Lys Gln Pro Ala Ser Gln Pro Gln Gly Asp Pro Thr Gly Pro
    130                 135                 140

Lys Glu
145

<210> SEQ ID NO 11
```

```
<211> LENGTH: 146
<212> TYPE: PRT
<213> ORGANISM: Artificial Sequence
<220> FEATURE:
<223> OTHER INFORMATION: Tat-CD4 fusion protein

<400> SEQUENCE: 11

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Gly Leu Gly Ile Ser Tyr Gly
        35                  40                  45

Arg Lys Thr Cys Thr Ala Ser Gln Lys Lys Ser Ile Gln Phe His Trp
    50                  55                  60

Lys Asn Ser Asn Gln Ile Lys Ile Leu Gly Asn Gln Gly Ser Phe Leu
65                  70                  75                  80

Thr Lys Gly Pro Ser Lys Leu Asn Asp Arg Ala Asp Ser Arg Arg Ser
                85                  90                  95

Leu Trp Gln Gly Asn Phe Pro Leu Ile Ile Lys Asn Leu Lys Ile Glu
            100                 105                 110

Asp Ser Asp Thr Tyr Ile Cys Glu Pro Asp Ser Glu Val His Gln Ser
        115                 120                 125

Leu Pro Lys Gln Pro Ala Ser Gln Pro Gln Gly Asp Pro Thr Gly Pro
    130                 135                 140

Lys Glu
145

<210> SEQ ID NO 12
<211> LENGTH: 86
<212> TYPE: PRT
<213> ORGANISM: Human immunodeficiency virus

<400> SEQUENCE: 12

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 13
<211> LENGTH: 101
<212> TYPE: PRT
<213> ORGANISM: Human immunodeficiency virus

<400> SEQUENCE: 13

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Gly Leu Gly Ile Ser Tyr Gly
        35                  40                  45
```

```
Arg Lys Lys Arg Arg Gln Arg Arg Ala Pro Pro Asp Ser Glu Val
    50              55                  60
His Gln Val Ser Leu Pro Lys Gln Pro Ala Ser Gln Pro Gln Gly Asp
65              70                  75                  80
Pro Thr Gly Pro Lys Glu Ser Lys Lys Lys Val Glu Arg Glu Thr Glu
                85                  90                  95
Thr Asp Pro Val His
            100
```